United States Patent
Matsuo

(10) Patent No.: US 9,345,390 B2
(45) Date of Patent: May 24, 2016

(54) ENDOSCOPE FLEXIBLE TUBE AND ENDOSCOPE DEVICE

(75) Inventor: Shigeki Matsuo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 2718 days.

(21) Appl. No.: 11/884,340

(22) PCT Filed: Feb. 10, 2006

(86) PCT No.: PCT/JP2006/302379
§ 371 (c)(1),
(2), (4) Date: Aug. 14, 2007

(87) PCT Pub. No.: WO2006/085620
PCT Pub. Date: Aug. 17, 2006

(65) Prior Publication Data
US 2010/0168519 A1    Jul. 1, 2010

(30) Foreign Application Priority Data
Feb. 14, 2005   (JP) ................. 2005-036969

(51) Int. Cl.
| | |
|---|---|
| *A61B 1/00* | (2006.01) |
| *A61B 1/04* | (2006.01) |
| *A61M 25/00* | (2006.01) |
| *A61B 1/005* | (2006.01) |
| *G02B 23/24* | (2006.01) |
| *G02B 23/26* | (2006.01) |
| *A61B 1/31* | (2006.01) |

(52) U.S. Cl.
CPC ........... *A61B 1/0055* (2013.01); *A61B 1/00071* (2013.01); *A61B 1/00078* (2013.01); *G02B 23/2476* (2013.01); *G02B 23/26* (2013.01); *A61B 1/31* (2013.01)

(58) Field of Classification Search
USPC ......... 600/138–152, 104, 106, 107, 114–116, 600/127–130, 433–435; 604/523–528, 604/95.01–95.05; 606/1
See application file for complete search history.

(56) References Cited

U.S. PATENT DOCUMENTS

| | | | |
|---|---|---|---|
| 3,060,972 A | 10/1962 | Sheldon | |
| 4,351,323 A * | 9/1982 | Ouchi et al. | ............. 600/142 |

(Continued)

FOREIGN PATENT DOCUMENTS

| | | |
|---|---|---|
| DE | 103 08 902 A1 | 12/2003 |
| JP | 58-49132 | 3/1983 |

(Continued)

*Primary Examiner* — Ryan Henderson
(74) *Attorney, Agent, or Firm* — Scully, Scott, Murphy & Presser, P.C.

(57) ABSTRACT

In an endoscope flexible tube and an endoscope device of the present invention, an endoscope flexible tube which exhibits flexibility to be inserted into a body cavity includes a bending portion formed at a distal end side, a first flexible tube portion connected in series to a proximal end of the bending portion, and a second flexible tube portion connected in series to a proximal end of the first flexible tube portion. When the bending portion and the first flexible tube portion pass a flexed portion of the body cavity, a curvature radius of the first flexible tube portion which is passively bent under a predetermined force is set to be larger than a curvature radius of the bending portion in a maximum bent state.

4 Claims, 21 Drawing Sheets

(56) References Cited

U.S. PATENT DOCUMENTS

| | | | |
|---|---|---|---|
| 4,807,598 A * | 2/1989 | Hasegawa | 600/140 |
| 5,386,816 A | 2/1995 | Inoue et al. | |
| 5,885,208 A | 3/1999 | Moriyama | |
| 2002/0028984 A1* | 3/2002 | Hayakawa et al. | 600/139 |
| 2002/0128537 A1* | 9/2002 | Watanabe et al. | 600/117 |
| 2003/0023142 A1 | 1/2003 | Grabover et al. | |
| 2004/0044270 A1* | 3/2004 | Barry | 600/142 |

FOREIGN PATENT DOCUMENTS

| | | |
|---|---|---|
| JP | 63-249536 | 10/1988 |
| JP | 1-22641 | 7/1989 |
| JP | 04-261635 | 9/1992 |
| JP | 05-095895 | 4/1993 |
| JP | 09-024020 | 1/1997 |
| JP | 2000-342517 | 12/2000 |
| JP | 2002-000552 | 1/2002 |
| JP | 2002-330924 | 11/2002 |

* cited by examiner

ENDOSCOPE FLEXIBLE TUBE AND ENDOSCOPE DEVICE

TECHNICAL FIELD

The present invention relates to an endoscope flexible tube which exhibits flexibility and an endoscope device.

BACKGROUND ART

Generally in the medical field, the endoscope has been used by inserting its thin and long insertion portion into a body cavity for the purpose of observing the internal organ within the body cavity such as the large intestine, or performing various types of treatment using the treatment instrument inserted into the treatment instrument channel if required. The insertion portion of the endoscope includes a distal end portion, a bending portion and a flexible tube portion in the order from the distal end.

When the insertion portion of the endoscope is inserted into the body cavity, the user, for example, the operator grasps the flexible tube portion to perform a predetermined operation of an operation knob provided on an operation portion of the endoscope while pushing the flexible tube portion into the body cavity such that the bending portion is bent toward a desired direction. The insertion portion of the endoscope has been made into various forms so as to be inserted into the body cavity further smoothly.

For example, the endoscope disclosed in Japanese Unexamined Patent Application Publication No. 58-49132 (Patent Document 1) has its distal end portion of the insertion portion provided with a first bending portion and a second bending portion connected in series in the order from the distal end portion. The first bending portion includes a series of plural bending pieces inside so as to be bent through the predetermined operation of the operation portion.

The insertion portion of the endoscope disclosed in Utility Model Application Publication No. 1-22641. (Patent Document 2) is provided with a first bending portion which can be externally bent toward four directions, and a readily flexural second bending portion provided with the stay coil and the node ring so as to be bent toward four directions, which are connected in series in the order from the distal end side.

When the insertion portion of the endoscope as disclosed in Patent Documents 1 and 2 passes the flexed portion within the body cavity, the second bending portion is bent while following the bending state of the first bending portion which has been subjected to the bending operation along the body cavity wall. The second bending portion of the endoscope may be bent at the smaller curvature radius than that of the first bending portion depending on the insertion condition. The second bending portion may abut on the body cavity wall under the force applied by the operator to push the insertion portion, and is brought into the state where a large flexed state is locally observed.

The second bending portion in the aforementioned flexed state presses the flexed body cavity wall which may be flexed further acutely in accordance with the force pushed by the operator. This may cause the second bending portion to be stuck with the acutely flexed body cavity. In the thus acutely flexed body cavity, the resistance of the body cavity wall against the second bending portion is increased to make it difficult for the insertion portion to be inserted into the flexed portion of the body cavity.

In the aforementioned case, unnecessarily excessive load is exerted to the body cavity to be stretched to the level more than necessary. This may impose not only the burden but also the pain on the patient who receives the endoscopic inspection.

In view of the aforementioned disadvantageous state, it is an object of the present invention to provide an endoscope which suppresses the resistance generated when the insertion portion passes a flexed portion of the body cavity during the endoscopic inspection so as to improve the insertion performance of the insertion portion, and to alleviate the burden and the pain imposed on the patient.

DISCLOSURE OF INVENTION

Means for Solving the Problem

A first aspect of the present invention provides an endoscope flexible tube which exhibits flexibility to be inserted into a body cavity including a bending portion formed at a distal end side, a first flexible tube portion connected in series to a proximal end of the bending portion, and a second flexible tube portion connected in series to a proximal end of the first flexible tube portion. When the bending portion and the first flexible tube portion pass a flexed portion of the body cavity, a curvature radius of the first flexible tube portion which is passively bent under a predetermined force is set to be larger than a curvature radius of the bending portion in a maximum bent state.

A second aspect of the present invention provides an endoscope flexible tube which exhibits flexibility to be inserted into a body cavity including a bending portion formed at a distal end side which is brought into a maximum bent state with a first curvature radius, a first flexible tube portion connected in series to a proximal end of the bending portion, which is brought into the maximum bent state with a second curvature radius, and a second flexible tube portion connected in series to a proximal end of the first flexible tube portion. The second curvature radius is set to be larger than the first curvature radius.

A third aspect of the present invention provides an endoscope flexible tube which exhibits flexibility to be inserted into a body cavity including a bending portion formed at a distal end side which is brought into a maximum bent state with a first curvature radius, a first flexible tube portion connected in series to a proximal end of the bending portion, which is brought into a maximum bent state with a second curvature radius larger than the first curvature radius, and a second flexible tube portion connected in series to a proximal end of the first flexible tube portion, which is brought into a maximum bent state with a third curvature radius larger than the second curvature radius.

The endoscope according to a fourth aspect of the present invention includes the endoscope flexible tube according to any one of the first to the third aspects as described above.

BEST MODE FOR CARRYING OUT THE INVENTION

First Embodiment

Figure 1:
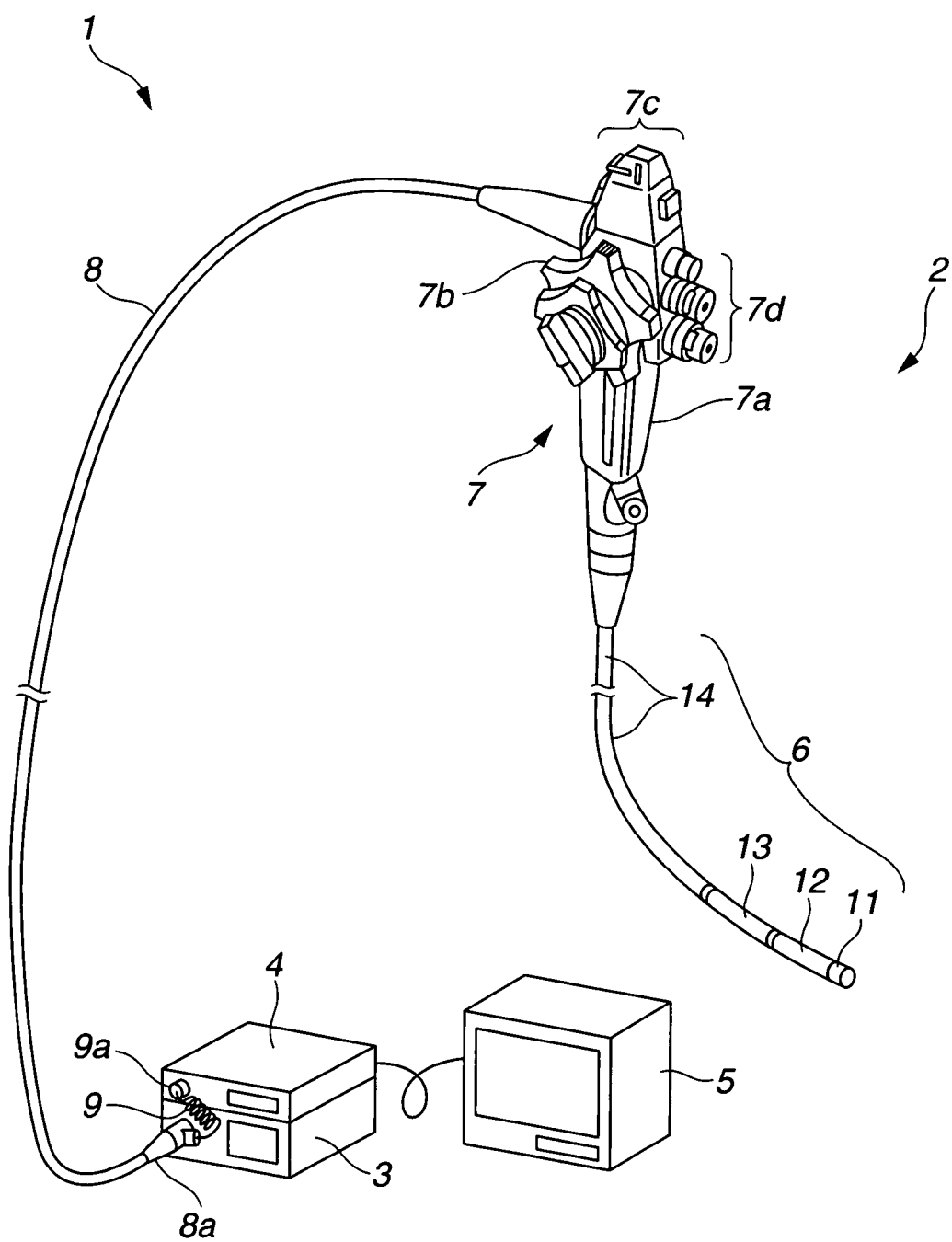
FIG. 1 is a view showing an entire configuration of an endoscope device with an endoscope according to a first embodiment.

The first embodiment of the present invention will be explained referring to the drawings.

FIG. 1 is a view showing an entire configuration of an endoscope device with an endoscope.

Referring to FIG. 1, an endoscope device 1 includes an electronic endoscope equipped with not shown image pickup means (hereinafter referred to an endoscope) 2, a light source device 3 for supplying illumination light, a processor 4 for generating a video signal based on an electric signal transmitted from the image pickup means of the endoscope 2, and a monitor 5 as a display unit for displaying an endoscopic image in response to the video signal.

The endoscope 2 according to the embodiment mainly includes an insertion portion 6 as an endoscope flexible tube which is long enough to be inserted into the body cavity, an operation portion 7 positioned at the proximal end side of the insertion portion 6, and a universal cord 8 which extends from one side portion of the operation portion 7.

The operation portion 7 includes a grasping portion 7a, a bending operation knob 7b, various switches 7c used for commanding to release the image pickup means, and various buttons 7d such as an air/water feed button.

The universal cord 8 has its distal end portion at the extended side provided with an endoscope connector 8a detachably connected to the light source device 3 as an external unit. An electric cable 9 having an electric connector 9a connected to the processor 4 as the external unit extends from the endoscope connector 8a.

The insertion portion 6 of the endoscope 2 includes a distal end configuration portion 11, a bending portion 12, a curvature transition portion 13 as a first flexible tube portion, a force quantity transmission portion 14 as a second flexible tube portion, and a connector portion to be described later.

A predetermined pressing force applied to the force quantity transmission portion 14 is transmitted to the curvature transition portion 13 when the insertion portion 6 is inserted into the body cavity. Upon reception of the force, the curvature transition portion 13 inserted into the body cavity is passively bent in abutment on the flexed body cavity wall.

The curvature radius of the curvature transition portion 13 in the maximum bent state is larger than the curvature radius of the bending portion 12 in the maximum bent state where it is in the bending operation state or the passive bent state. The force quantity transmission portion 14 is passively bent under the predetermined pressing force.

The curvature radius of the curvature transition portion 13 in the maximum bent state is set to be smaller than that of the force quantity transmission portion 14 in the maximum bent state where it is passively bent under the predetermined pressing force.

The insertion portion 6 includes the bending portion 12, the curvature transition portion 13 and the force quantity transmission portion 14 arranged in the order from the distal end thereof such that the bending radius/curvature undergoes the stepwise transition when the insertion portion is brought into the maximum bent state. The bent state of the insertion portion 6 as described above will be described later in detail.

The distal end configuration portion 11 contains an image pickup device serving as image pickup means, for example, CCD, CMOS, a circuit substrate for driving the image pickup device, and a not shown image pickup unit formed of an observation optical system. The distal end configuration portion 11 is equipped with the distal end portion of a light guide which allows the illumination light to pass for illuminating the observation site in the body cavity, and contains an illumination unit including the light guide, the illumination optical system and the like.

Figure 2:
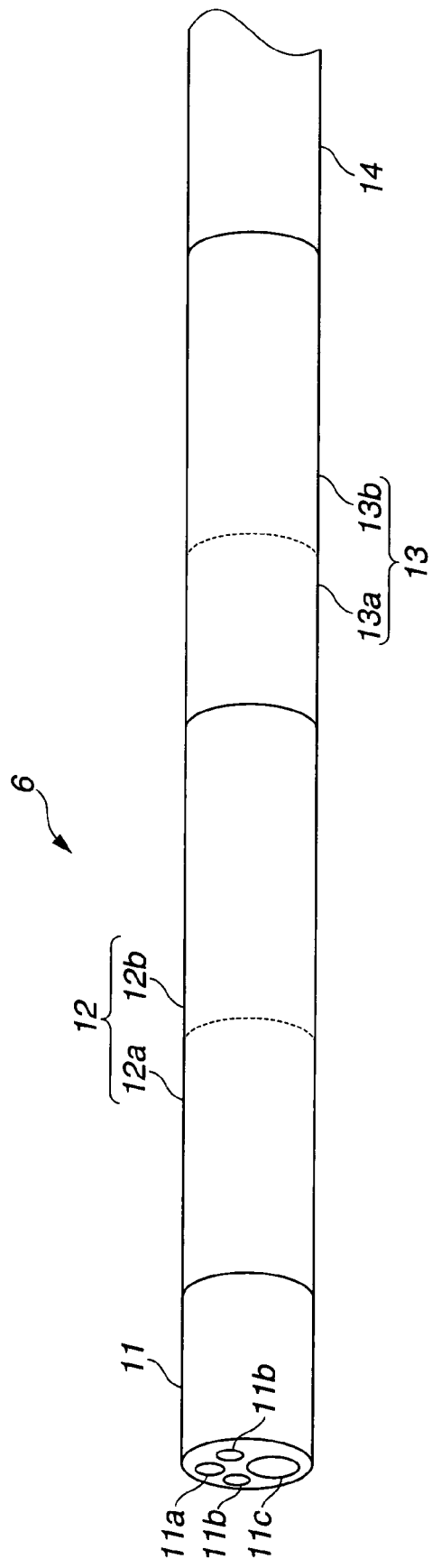
FIG. 2 is a view representing a distal end portion of an insertion portion of the endoscope shown in FIG. 1.
Figure 3:
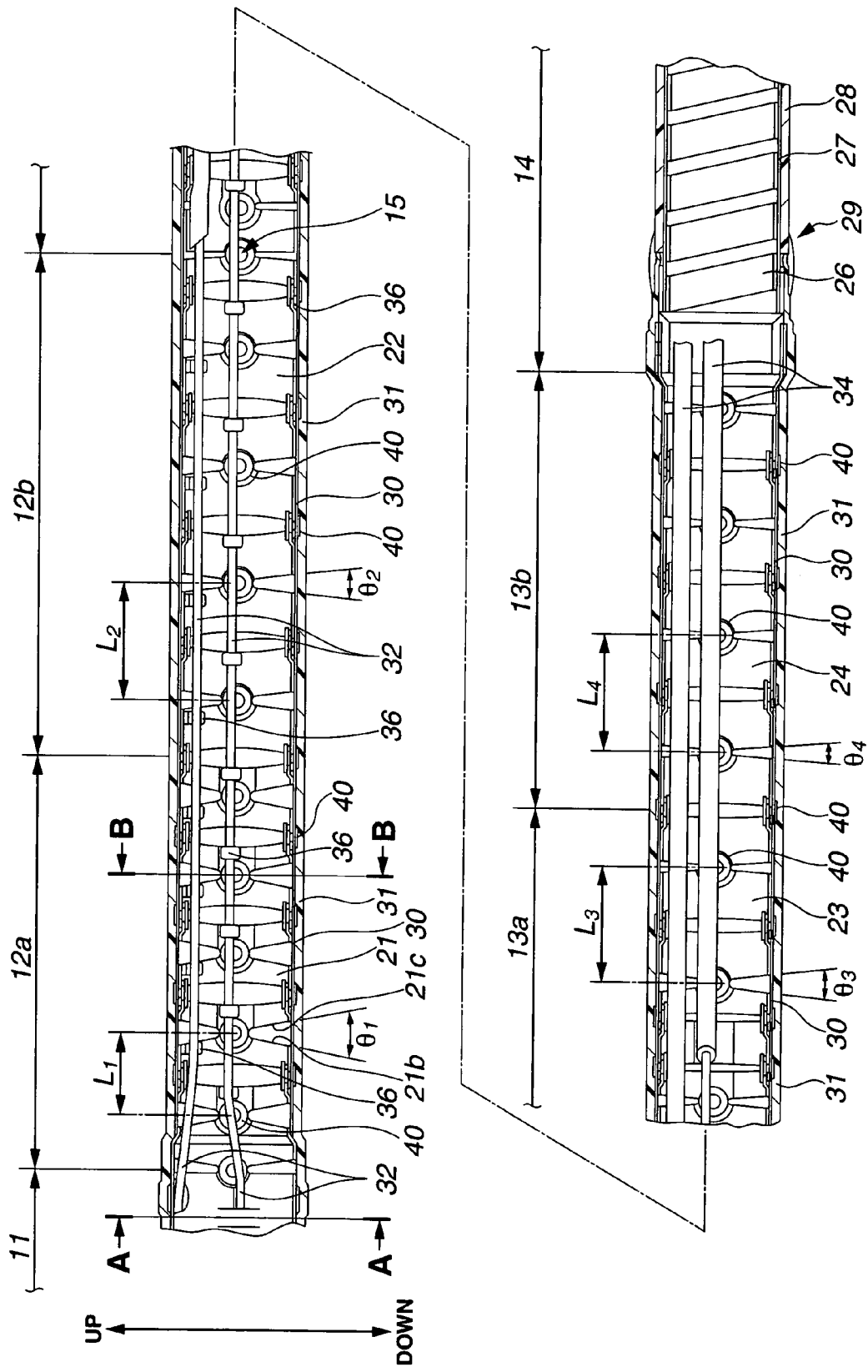
FIG. 3 is a sectional view showing a section of the distal end portion of the insertion portion of the endoscope shown in FIG. 1, which has been cut in the longitudinal direction.
Figure 4:
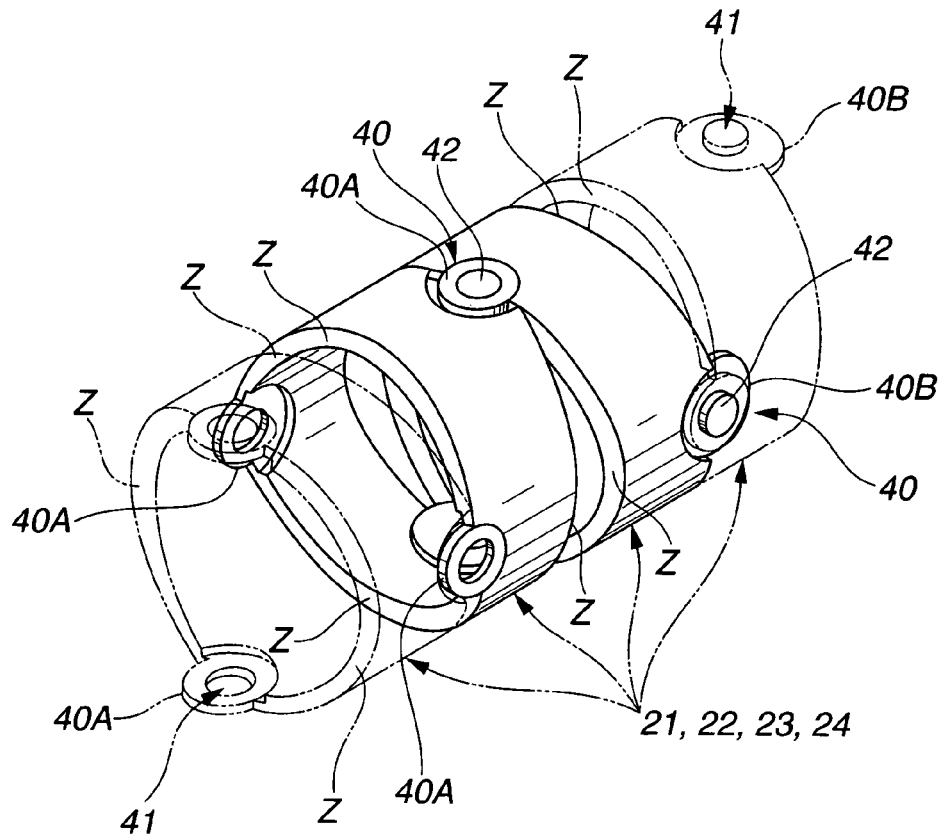
FIG. 4 is a perspective view representing respective pieces of the insertion portion shown in FIG. 3.
Figure 5:
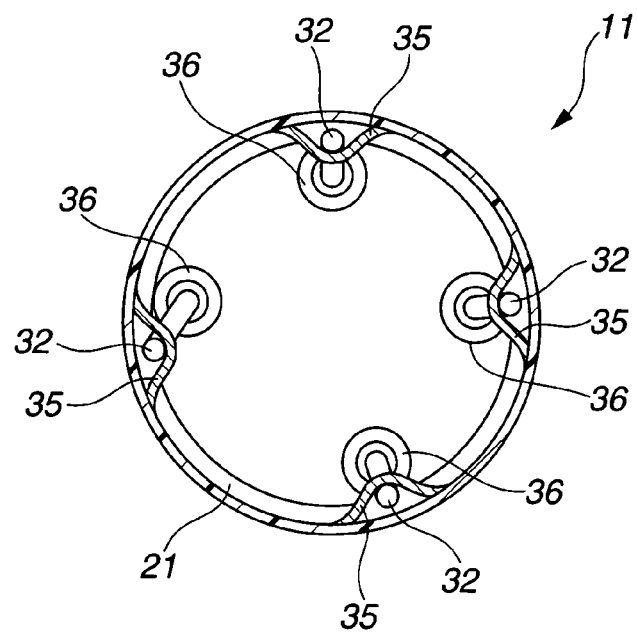
FIG. 5 is a sectional view of the distal end portion taken along line A-A shown in FIG. 3.
Figure 6:
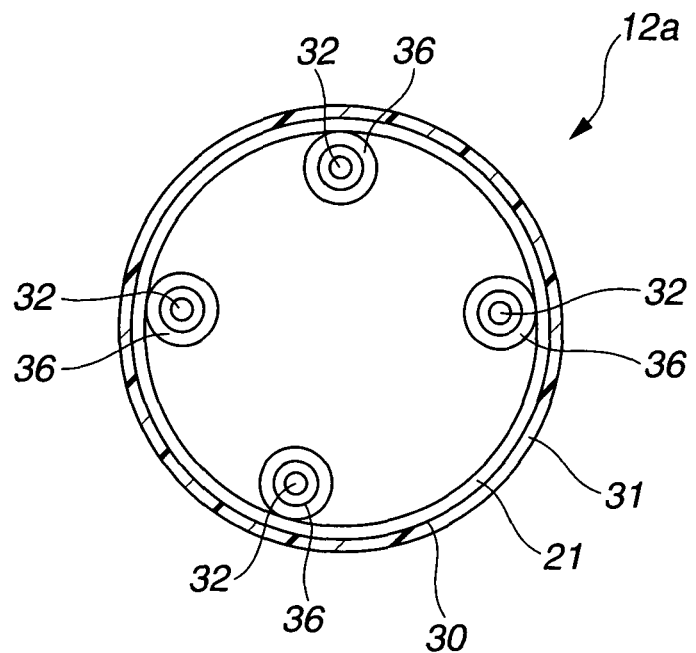
FIG. 6 is a sectional view of a first bending portion taken along line B-B shown in FIG. 3.

Each structure of the distal end configuration portion, the bending portion, the curvature transition portion and the flexible tube portion of the insertion portion will be described referring to FIGS. 2 to 6. FIG. 2 is a view which represents the distal end portion of the insertion portion. FIG. 3 is a sectional view showing the section of the distal end portion of the insertion portion, which has been cut in the longitudinal direction. FIG. 4 is a perspective view intended to explain with respect to each piece. FIG. 5 is a sectional view of the distal end portion taken along line A-A shown in FIG. 3. FIG. 6 is a sectional view of the first bending portion taken along line B-B shown in FIG. 6.

Referring to FIG. 2, the distal end configuration portion 11 provided at the distal end of the insertion portion 6 has its distal end surface provided with an observation window 11a equipped with an observation lens, two illumination windows 11b equipped with the illumination lens and the like, for example, and an opening 11c of a forceps channel through which the forceps and the like as the treatment instrument is inserted.

The bending portion 12 connected in series to the proximal end side of the distal end configuration portion 11 is formed of a first bending portion 12a and a second bending portion 12b in the order from the distal end side. The length of the first bending portion 12a in the direction of the insertion axis is in the range from approximately 30 to 35 mm. The length of the second bending portion 12b in the direction of the insertion axis is in the range from approximately 40 to 45 mm, for example.

The curvature transition portion 13 is formed of a first curvature transition portion 13a and a second curvature transition portion 13b in the order from the distal end side. The length of the first curvature transition portion 13a in the direction of the insertion axis is in the range from approximately 30 to 40 mm. The length of the second curvature transition portion 13b in the direction of the insertion axis is in the range from approximately 30 to 40 mm, for example.

Referring to FIG. 3, the bending portion 12 is formed of a plurality of bending pieces (bending nodal rings) which are rotatably connected in series to be described later. The curvature transition portion 13 is formed of a plurality of curvature regulation pieces (curvature regulation node rings) which are rotatably connected in series to be described later.

In the embodiment, the piece having a wire guide to be described later will be referred to as the bending piece, and the piece having no wire guide will be referred to as the curvature regulation piece. In other words, the plurality of bending pieces in the bending portion 12 include wire guides, and the plurality of curvature regulation pieces in the curvature transition portion 13 do not include the wire guides.

The connection between the bending portion 12 and the curvature transition portion 13 is rotatably made at the inside the respective boundaries such that each rotating direction of the bending piece and the curvature regulation piece accord with each other. More specifically, each portion at which both the rotating bending piece and the curvature regulation piece are connected between the bending portion 12 and the curvature transition portion 13 of the insertion portion 6 in the endoscope 2 for the vertical bending as shown in FIG. 3 will be referred to as a connector portion 15. In the endoscope 2 according to the embodiment, the bending portion 12 and the curvature transition portion 13 are allowed to bend in four directions, that is, the upward, downward, leftward and rightward. The portion at which both the rotating bending piece and the curvature regulation piece are connected for bending in the lateral direction substantially orthogonal to the vertical direction may also be the joint portion. That is, the endoscope 2 according to the embodiment includes two connector portions 15 having the respective bending pieces and the curvature regulation pieces are connected.

In the embodiment, the respective bending piece and the curvature regulation piece at the boundary between the bending portion 12 and the curvature transition portion 13 may be connected through fixing rather than the rotatable manner.

The plural bending pieces and the curvature regulation pieces are covered with a bending braid 30 formed by braiding a thin wire into a cylindrical shape, and further covered with an outer coat 31 as a first outer tube body for holding fluid tightness on the bending braid 30 so as to form the bending portion 12 and the curvature transition portion 13.

The bending braid 30 and the outer coat 31 may be integrally coated across the whole length of the bending portion 12 and the curvature transition portion 13. Alternatively, they may be coated on the bending portion 12 and the curvature transition portion 13 independently. The bending portion 12 and the curvature transition portion 13 are coated with the outer coat 31 which exhibits a predetermined flexural rigidity so as to equalize the respective flexural rigidity.

The thickness of the portion of the outer coat 31 which covers the bending portion 12 may be larger than that of the portion of the outer coat 31 which covers the curvature transition portion 13. In other words, the portion of the outer coat 31 which coats the curvature transition portion 13 may be smaller than that of the portion of the outer coat 31 which covers the bending portion 12. Accordingly, the flexural rigidity of the portion of the outer coat 31 that covers the curvature transition portion 13 may be set lower than that of the, portion of the outer coat 31 that covers the bending portion 12.

Meanwhile, the thickness of the portion of the outer cover 31 which covers the curvature transition portion 13 may be larger than that of the portion of the outer coat 31 which covers the bending portion 12. Accordingly, the flexural rigidity of the portion of the outer coat 31 which covers the curvature transition portion 13 may be set to be higher than that of the portion of the outer coat 31 which covers the bending portion 12.

The plural first bending pieces 21 are connected in series in the first bending portion 12a. Meanwhile, the plural bending pieces 22 are connected in series in the second bending portion 12b. The first bending piece 21 at the distal end portion is provided at the proximal end side of the distal end configuration portion 11.

The plural first curvature regulation pieces 23 are connected in series in the first curvature transition portion 13a. Meanwhile, the plural second curvature regulation pieces 24 are connected in series in the second curvature transition portion 13b.

Referring to FIG. 4, the bending pieces 21, 22 and the curvature regulation pieces 23, 24 are a plurality of curvature regulation bodies each formed of a short substantially cylindrical tube (rigid tubular member). Each end, that is, each distal end side of the bending pieces 21, 22 and the curvature regulation pieces 23, 24 is provided with a pair of pivotally supporting portions 40A so as to be rotatably connected to the adjacent piece. The pair of pivotally supporting portions 40A are disposed at the position which separates the circumference of the respective bending pieces 21, 22 and the curvature regulation pieces 23, 24 into two sections, that is, at the positions displaced at 180° in the circumferential direction around the insertion axis.

Likewise the aforementioned end side, each of the other ends of the bending pieces 21, 22 and the curvature regulation pieces 23, 24, that is, the proximal end side is provided with a pair of the pivotally supporting portions 40B displaced by the plate thickness thereof at the inner periphery. The pivotally supporting portions 40A and 40B at one end side and the other end side of the respective bending pieces 21, 22, and the curvature regulation pieces 23, 24 are overlapped with each other, and each pivot member 42 such as a rivet is inserted into a hole 41 formed in the pivotally supporting portions 40A and 40B so as to be axially supported.

The pair of pivotally supporting portions 40A at one end of each of the bending pieces 21, 22 and the curvature regulation pieces 23, 24 are provided at the position displaced at 90° around the insertion axis with respect to the pair of the pivotally supporting portions 40B at the other end side. In other words, the pair of the pivotally supporting portion 40A at one end side of each of the bending pieces 21, 22 and the curvature regulation pieces 23, 24 are provided at the position orthogonal to the line formed by connecting axes of the respective pivot members 42, the line formed by connecting the pair of the pivotally supporting portions 40B at the other end side, and the insertion axis.

The thus linked bending pieces 21, 22 and the curvature regulation pieces 23, 24 are connected such that one end side is rotatable in two directions around the axis of the pivot member 42 of the pivotally supporting portion 40A, and the other end side is rotatable in the two directions around the axis of the pivot member 42 of the pivotally supporting portion 40B orthogonal to the aforementioned two directions with respect to the insertion axis. In the explanation of the embodiment, the portion formed of the pivotally supporting portions 40A and 40B, and the pivot member 42 will be referred to as a joint portion 40.

The bending pieces 21, 22 and the curvature regulation pieces 23, 24 are annular members linked to the adjacent pieces via the joint portions 40. As described above, they are annular members each processed into a triangular shape having the axial length made shorter, and the pivotally supporting portions 40A and 40B each as an edge portion protrude from both end surfaces so as to face one another.

The bending pieces 21, 22 and the curvature regulation pieces 23, 24 are linked such that a portion of each end surface (for example, an end surface 21b of the first bending piece 21 shown in FIG. 3) abuts on a portion of the opposite surface of the adjacent piece (for example, an end surface 21c of the first bending piece 21 shown in FIG. 3) when the respective end surface of one end side or the other end side is rotated by the pivotally supporting portions 40A and 40B.

In the description hereinafter, the portion where the end surface abuts on the opposite surface of the adjacent piece accompanied with each rotation of the pieces 21, 22, 23 and 24 will be referred to as an abutment portion Z (see FIG. 4). The abutment portions Z exist on both end surfaces of the pieces 21, 22, 23, and 24 at the positions displaced at 90° in the direction around the insertion axis with respect to the two joint portions 40 of the linked pieces 21, 22, 23 and 24. Each of the pieces 21, 22, 23 and 24 has both ends notched to form a triangular shape with end surfaces positioned to the center of the outer surface such that the abutment portion Z is apart from the abutment portion Z of the adjacent piece by a predetermined distance.

The bending pieces 21, 22 and the curvature regulation pieces 23, 24 when the bending portion 12 and the curvature transition portion 13 are in substantially the linear state are linked such that a predetermined gap is formed between the abutment portions Z in abutment state as described above. Each shape of both end surfaces of the bending pieces 21, 22 and the curvature regulation pieces 23, 24 according to the embodiment is not limited to the shape configured into the triangle with both end surfaces directed to the center of the outer shape, but may be arbitrarily configured so long as a predetermined gap is formed between the adjacent abutment portions Z in the linked state.

The respective linkages among the bending pieces 21, 22 and the curvature regulation pieces 23, 24 will be described referring to FIG. 3.

When the insertion axis of the first bending portion 12a is in the linear state, the angle defined by the lines formed by connecting the abutment portions Z (see FIG. 4) with the apex, that is, the common rotating axial center of the two first bending pieces 21 rotated to be in the abutment state is set to a predetermined angle θ1. The pair of joint portions 40 having the parallel pivot members 42 in the axial direction in the first bending portion 12a is configured such that the axes of the pivot members 42 are provided at a predetermined distance L1 in the longitudinal direction of the first bending portion 12a.

When the insertion axis of the second bending portion 12b is in the linear state, the angle defined by the lines formed by connecting the abutment portions Z (see FIG. 4) with the apex, that is, the common rotating axial center of the two second bending pieces 22 rotated to be in the abutment state is set to a predetermined angle θ2. The pair of joint portions 40 having the parallel pivot members 42 in the axial direction in the second bending portion 12b is configured such that the axes of the pivot members 42 are provided at a predetermined distance L2 in the longitudinal direction of the second bending portion 12b.

When the insertion axis of the first curvature transition portion 13a is in the linear state, the angle defined by the lines formed by connecting the abutment portions Z (see FIG. 4) with the apex, that is, the common rotating axial center of the two first curvature regulation pieces rotated to be in the abutment state is set to a predetermined angle θ3. The pair of joint portions 40 having the parallel pivot members 42 in the axial direction in the first curvature transition portion 13a is configured such that the axes of the pivot members 42 are provided at a predetermined distance L3 in the longitudinal direction of the first curvature transition portion 13a.

When the insertion axis of the second curvature transition portion 13b is in the linear state, the angle defined by the lines formed by connecting the abutment portions Z (see FIG. 4) with the apex, that is, the common rotating axial center of the two second curvature regulation pieces 24 rotated to be in the abutment state is set to a predetermined angle θ4. The pair of joint portions 40 having the parallel pivot members in the axial direction in the second curvature transition portion 13b is configured such that the axes of the pivot members 42 are provided at a predetermined distance L4 in the longitudinal direction of the second curvature transition portion 13.

The joint portion between the first bending portion 12a and the second bending portion 12b is rotatably linked with the pair of the joint portions 40 of the first bending piece 21 at the most proximal end and the pair of the joint portions 40 of the second bending piece 22 at the most distal end. The joint portion between the first curvature transition portion 13a and the second curvature transition portion 13b is rotatably linked with the pair of the joint portions 40 of the first curvature regulation piece 23 at the most proximal end and the pair of the joint portions 40 of the second curvature regulation piece 24 at the most distal end.

As described above, the second bending piece 22 at the most proximal end and the first curvature regulation piece 23 at the most distal end are rotatably linked at the boundary portion between the second bending portion 12b and the first curvature transition portion 13a with the pair of the joint portions 40 of the second bending piece 22 at the most proximal end and the pair of the joint portions 40 of the first curvature regulation piece 23 at the most distal end.

A flex tube 26 as a helical tube is inserted into the force quantity transmission portion 14. Likewise the bending portion 12 and the curvature transition portion 13, the outer circumference of the flex tube 26 is covered with a braid 27. The outer circumference of the braid 27 is further covered with an outer coat 28 as a second outer tube which exhibits lower flexibility, that is, higher flexural rigidity than that of the outer coat 31.

The force quantity transmission portion 14 is structured to have the lower flexibility, in other words, higher flexural rigidity compared with those of the bending portion 12 and the curvature transition portion 13 for the purpose of transmitting the pressing force at the proximal end side to the distal end portion of the insertion portion 6 sufficiently. A reel adhesion portion 29 is provided between the curvature transition portion 13 and the force quantity transmission portion 14 so as to adhere the outer coats 31 and 28 with the reel.

Four bending operation wires 32 (angle wires) are inserted into the insertion portion 6 such that the first bending portion 12a and the second bending portion 12b of the bending portion 12 are pulled and loosened to be bent from the distal end side. The bending operation wires 32 are inserted to be held with a wire guide 36 within the bending portion 12 where the proximal ends are inserted into a coil sheath 34 from the boundary portion between the second bending portion 12b and the first curvature transition portion 13a, respectively. The coil sheath 34 used herein has an incompressive structure where the wire is tightly wound like a pipe.

Referring to FIG. 5, the bending operation wires 32 have the respective distal end portions held and fixed with fix members 35 at four points each apart in the vertical and lateral directions shown in FIG. 5 at the proximal end side of the distal end configuration portion 11.

The bending operation wires 32 are linked with a not shown bending operation mechanism having the proximal end portion formed in the operation portion 7 (see FIG. 1) so as to be pulled or loosened alternately. The bending operation mechanism is linked to the bending operation knob 7b disposed on the operation portion 7.

The bending operation wires 32 are pulled and loosened through a predetermined operation of the bending operation knob 7b. Accordingly, the bending portion 12 may be bent in four directions through pulling and loosening of the four respective bending operation wires 32.

Referring to FIG. 6, two wire guides 36 through which the bending operation wires 32 are inserted to be held, respectively are fixed onto the inner peripheral surface of the portion of the first and the second bending pieces 21, 22 in the bending portion 12 adjacent to the proximal end surface with means such as welding.

Those two wire guides 36 are disposed on the inner peripheral surface substantially 180° displaced in the direction around the insertion axis that separates the circumference of each of the bending pieces 21, 22 into two equivalent portions at the position 90° displaced with respect to the pair of the joint portions 40 in the direction around the insertion axis. In other words, those two wire guides 36 are provided at positions on the inner peripheral surface of the bending pieces 21, 22 to separate the line formed by connecting those wires into two equivalent parts substantially orthogonal to the line formed by connecting the pair of the joint portions 40.

FIG. 6 is a sectional view showing the section of the first bending portion 12a when the first bending piece 21 is seen from the proximal end side.

In the explanation of the embodiment, the vertical direction shown in FIGS. 5 and 6 represents the direction orthogonal to the insertion axis of the insertion portion 6 shown in FIG. 3. The lateral direction shown in FIGS. 5 and 6 represents the horizontal direction orthogonal to both the vertical direction and to the insertion axis of the insertion portion 6 shown in FIG. 3.

The bending portion 12, the curvature transition portion 13 and the force quantity transmission portion 14 may be bent in the four directions in the up and down directions and right and left directions shown in FIG. 3, or the vertical and the lateral directions shown in FIGS. 5 and 6. As the curvature transition portion 13 and the force quantity transmission portion 14 are positively bent, they may be bent at 360° around the insertion axis without being limited to the four directions, that is, the up and down directions and right and left directions.

Each curvature and the curvature radius of the bending portion 12 and the curvature transition portion 13 in the maximum bent state will be described referring to FIGS. 7 to 10. The description with respect to the curvature and the curvature radius herein will be made using the sectional view of the second bending portion 12b of the bending portion 12 in the longitudinal direction.

Figure 7:
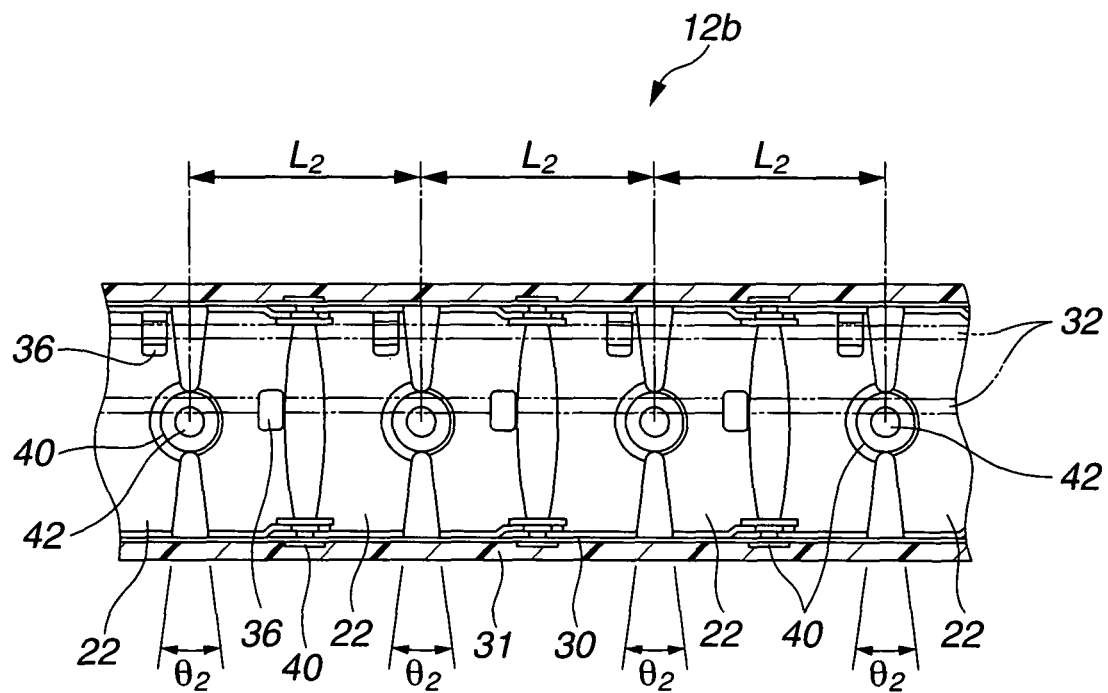
FIG. 7 is a sectional view showing a section of a second bending portion of the insertion portion with a linear insertion axis, which has been cut in the longitudinal direction shown in FIG. 3.
Figure 8:
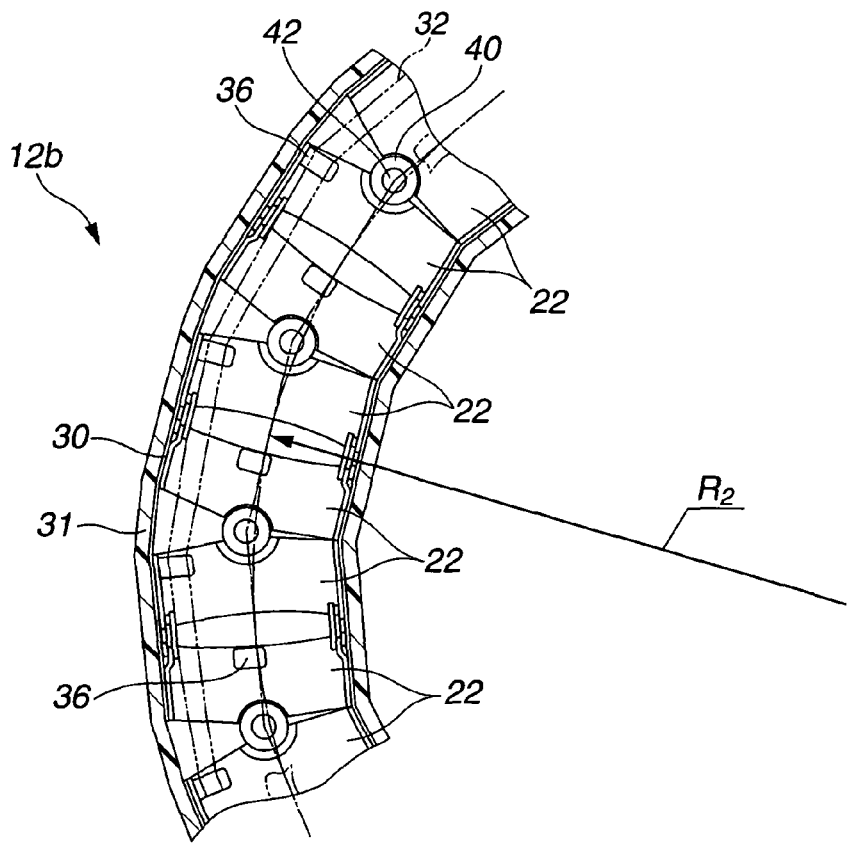
FIG. 8 is an enlarged view of the second bending portion shown in FIG. 3 in the state where it is in the maximum downward bent state.
Figure 9:
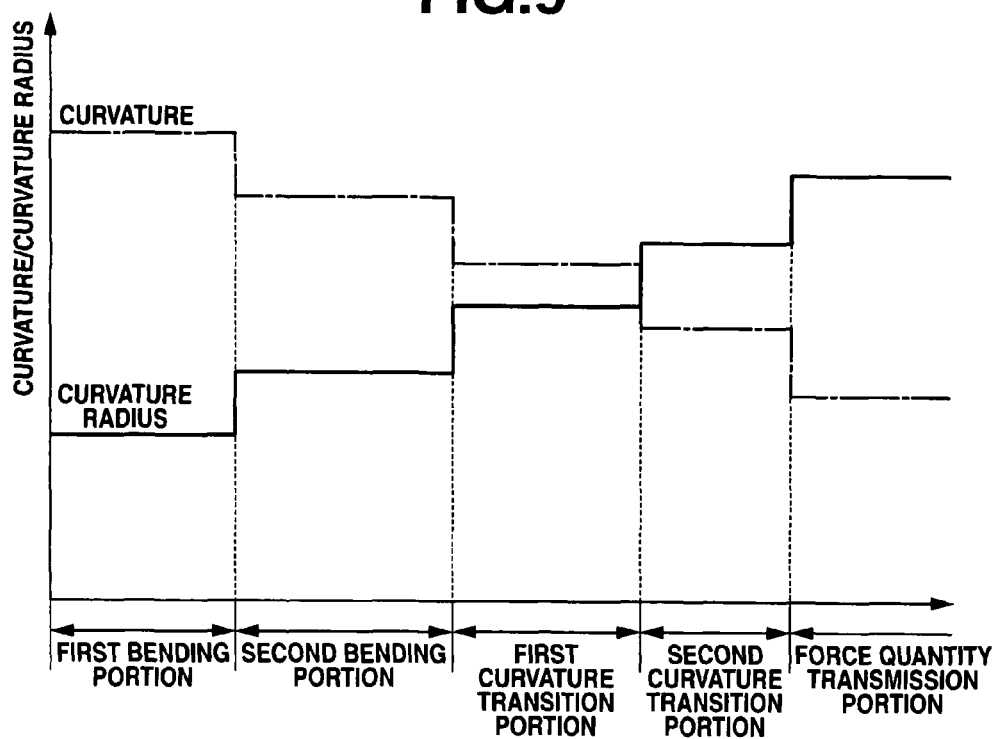
FIG. 9 is a graph showing each change in the curvature and the curvature radius of the respective bending portion, the curvature transition portion, and the flexible tube portion of the insertion portion shown in FIG. 3 at the respective insertion axes.
Figure 10:
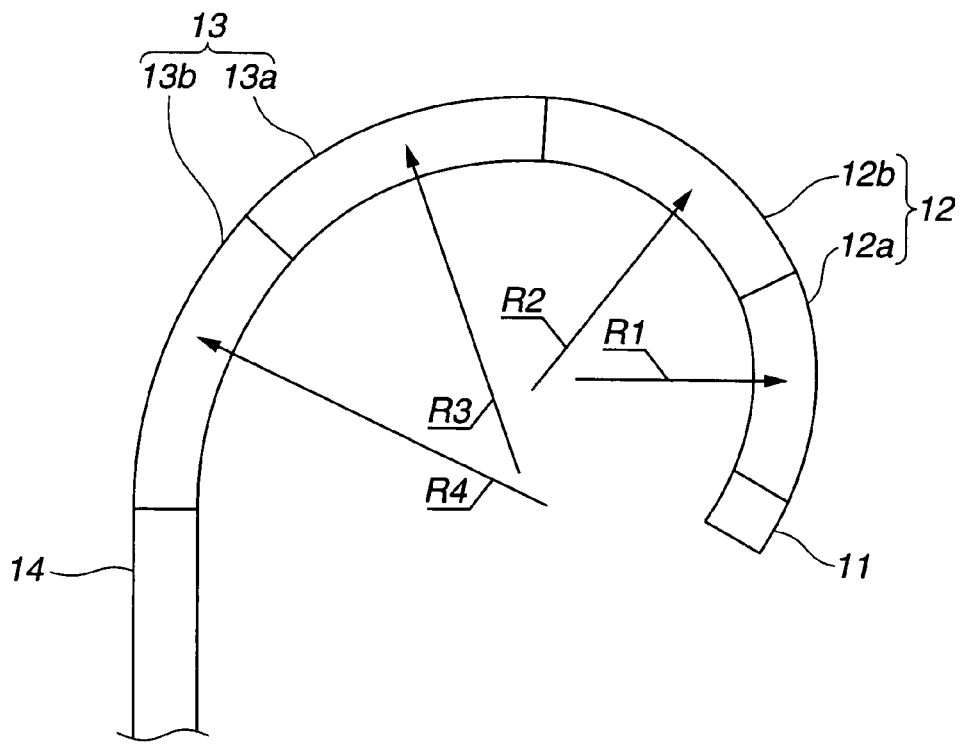
FIG. 10 is a side view of the bending portion, the curvature transition portion and the flexible tube portion of the insertion portion in the maximum bent state as shown in FIG. 3.
Figure 11:
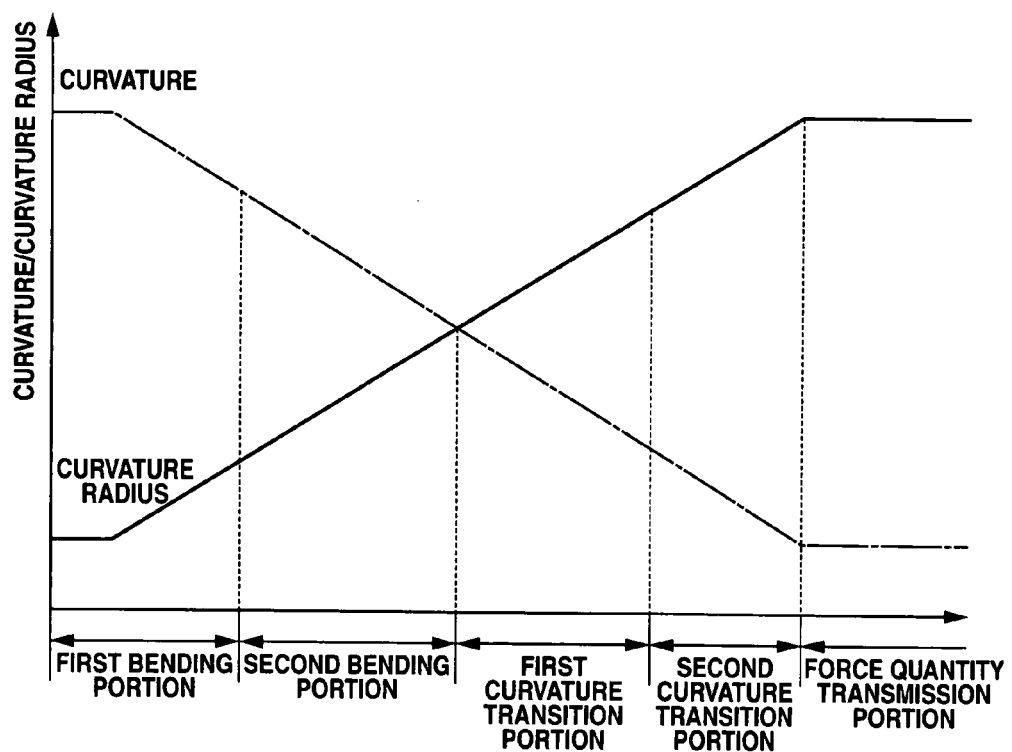
FIG. 11 is a graph showing each change in the curvature and the curvature radius of the respective bending portion, the curvature transition portion, and the flexible tube portion of the insertion portion shown in FIG. 3 at the respective insertion axes.

FIG. 7 is a sectional view showing the section of the second bending portion in substantially the linear state, which has been cut in the longitudinal direction. FIG. 8 is an enlarged view of the second bending portion shown in FIG. 3 in the maximum downward bent state. FIG. 9 is a graph showing each change in the curvature and the curvature radius of the bending portion, the curvature transition portion and the flexible tube portion at the insertion axis. FIG. 10 is a side view of the bending portion, the curvature transition portion and the flexible tube portion in the maximum bent state.

When the insertion axis of the second bending portion 12b is in the linear state, the angle defined by lines each formed by connecting the abutment portions Z (see FIG. 4) with the apex, that is, the common rotating axial center of the two second bending pieces 22 which rotate into the abutment state is set to a predetermined angle θ2. The pair of the joint portions 40 having the parallel pivot members 42 in the axial direction in the second bending portion 12b is configured such that the axes of the pivot members 42 are apart from each other by a predetermined distance L2 with respect to the longitudinal direction of the second bending portion 12b.

Referring to FIG. 8, the second bending portion 12b becomes the maximum bent state in the abutment state of the peripheral end portions (abutment portion Z) of the adjacent second bending pieces 22 at the bent side. More specifically, the second bending pieces 22 are moved in the direction around the axis of the pivot member 42 of the joint portion 40 as the rotating axis relative to the bending direction such that the peripheral end portions (abutment portions Z) inside the insertion axis which forms the arc as the second bending portion 12b bends get closer with each other. The respective peripheral end portions (abutment portions Z) of the second bending pieces 22 inside the insertion axis which forms the arc abut to prevent the rotation of the joint portion 40 around the axis.

The respective peripheral end portions (abutment portions Z) of the second bending piece 22 abut to allow the second bending portion 12b to function as a stopper such that the state where the rotation of the joint portion 40 around the axis is prevented is brought into the maximum bent state of the second bending portion 12b.

When the insertion axis of the second bending portion 12b is in the linear state, the curvature radius R2 of the second bending portion 12b in the maximum bent state is set in accordance with the relationship between the predetermined angle θ2 defined by the opposite surfaces of the two adjacent second bending pieces 22 and the distance L2 between the axes of the pivot members 42 in the parallel axial direction. That is, when the insertion axis of the second bending portion 12b is in the linear state, the curvature C2 as the inverse number of the curvature radius R2 of the insertion axis of the second bending portion 12b in the maximum bent state is also set in accordance with the relationship between the predetermined angle θ2 defined by the lines each formed by connecting the respective abutment portions Z (see FIG. 4) to the apex, that is, the common center of the rotating axis of the two adjacent second bending pieces 22, and the distance L2 between the axes of the pivot members 42 in the parallel axial direction with respect to the longitudinal direction of the second bending portion 12b.

The curvature C2 and the curvature radius R2 at the insertion axis of the second bending portion 12b in the maximum bent state may be derived from the following formula (1).

$$C2 = 1/R2 \approx (2 \tan \theta2/2)/L2 \tag{1}$$

The curvature C2 and the curvature radius R2 of the second bending portion 12b in the maximum bent state are set to approximately 1/33 (1/mm) and approximately 33 mm, respectively.

The curvature and the curvature radius of the first bending portion 12a, the first curvature transition portion 13a and the second curvature transition portion 13b in the maximum bent state are set in the aforementioned way.

When the peripheral ends (abutment portions Z) of the adjacent first bending pieces 21 in the bending direction are in the abutment state, the first bending portion 12a becomes in the maximum bent state. More specifically, the first bending pieces 21 are moved to the direction around the axis of the pivot members 42 of the joint portion 40 as the rotating axis relative to the bending direction such that the peripheral end portions (abutment portions Z) inside the insertion axis that forms the arc as the first bending portion 12a bends get closer. The first bending pieces 21 have the respective peripheral ends (abutment portion Z) inside the insertion axis that forms the arc brought into abutment state to prevent the rotation of the joint portion 40 in the direction around the axis.

As the respective peripheral ends (abutment portion Z) of the first bending pieces 21 are brought into the abutment state, the first bending portion 12a functions as the stopper to bring the state where the rotation around the axis of the joint portion 40 is prevented into the maximum bent state of the first bending portion 12a.

When the insertion axis of the first bending portion 12a is in the linear state, the curvature C1 and the curvature radius R1 at the insertion axis of the first bending portion 12a in the maximum bent state are set in accordance with the relationship between the predetermined angle θ1 defined by the lines each formed by connecting the respective abutment portions Z (see FIG. 4) and the apex, that is, the common rotating axial center of the two adjacent first bending pieces 21, and the distance L1 between the axes of the pivot members 42 in the parallel axial direction relative to the longitudinal direction of the first bending portion 12a.

The curvature C1 and the curvature radius R1 at the insertion axis of the first bending portion 12a in the maximum bent state may be derived from the following formula (2).

$$C1 = 1/R1 \approx (2 \tan \theta1/2)/L1 \tag{2}$$

The curvature C1 and the curvature radius R1 of the first bending portion 12a in the maximum bent state are set to approximately 1/16.5 (1/mm) and approximately 16.5 mm, respectively.

When the peripheral ends (abutment portions Z) of the adjacent first curvature regulation pieces 23 in the bending direction are in the abutment state, the first curvature transition portion 13a becomes in the maximum bent state. More specifically, the first curvature regulation pieces 23 are moved to the direction around the axis of the pivot members 42 of the joint portion 40 as the rotating axis relative to the bending direction such that the peripheral end portions (abutment portions Z) inside the insertion axis that forms the arc as the curvature transition portion 13a bends get closer. The first curvature regulation pieces 23 have the respective peripheral ends (abutment portion Z) inside the insertion axis that forms the arc brought into abutment state to prevent the rotation of the joint portion 40 in the direction around the axis.

As the respective peripheral ends (abutment portion Z) of the first curvature regulation pieces 23 are brought into the abutment state, the first curvature transition portion 13a functions as the stopper to bring the state where the rotation around the axis of the joint portion 40 is prevented into the maximum bent state of the first curvature transition portion 13a.

When the insertion axis of the first curvature transition portion 13a is in the linear state, the curvature C3 and the curvature radius R3 at the insertion axis of the first curvature transition portion 13a in the maximum bent state are set in accordance with the relationship between the predetermined angle θ3 defined by the lines each formed by connecting the respective abutment portions Z (see FIG. 4) and the apex, that is, the common rotating axial center of the two adjacent first curvature regulation pieces 23, and the distance L3 between the axes of the pivot members 42 in the parallel axial direction relative to the longitudinal direction of the first curvature transition portion 13a.

The curvature C3 and the curvature radius R3 at the insertion axis of the first curvature transition portion 13a in the maximum bent state may be derived from the following formula (3).

$$C3 = 1/R3 \approx (2 \tan \theta 3/2)/L3 \qquad (3)$$

The curvature C3 and the curvature radius R3 of the first curvature transition portion 13a in the maximum bent state are set to approximately 1/43 (1/mm) and to approximately 43 mm, respectively.

When the peripheral ends (abutment portions Z) of the adjacent second curvature regulation pieces 24 in the bending direction are in the abutment state, the second curvature transition portion 13b becomes in the maximum bent state. More specifically, the second curvature regulation pieces 24 are moved to the direction around the axis of the pivot members 42 of the joint portion 40 as the rotating axis relative to the bending direction such that the peripheral end portions (abutment portions Z) inside the insertion axis that forms the arc as the curvature transition portion 13b bends get closer. The second curvature regulation pieces 24 have the respective peripheral ends (abutment portion Z) inside the insertion axis that forms the arc brought into abutment state to prevent the rotation of the joint portion 40 in the direction around the axis.

As the respective peripheral ends (abutment portion Z) of the second curvature regulation pieces 24 are brought into the abutment state, the second curvature transition portion 13b functions as the stopper to bring the state where the rotation around the axis of the joint portion 40 is prevented into the maximum bent state of the second curvature transition portion 13b.

When the insertion axis of the second curvature transition portion 13b is in the linear state, the curvature C4 and the curvature radius R4 at the insertion axis of the second curvature transition portion 13b in the maximum bent state are set in accordance with the relationship between the predetermined angle θ4 defined by the lines each formed by connecting the respective abutment portions Z (see FIG. 4) and the apex, that is, the common rotating axial center of the two adjacent second curvature regulation pieces 24, and the distance L4 between the axes of the pivot members 42 in the parallel axial direction relative to the longitudinal direction of the second curvature transition portion 13b.

The curvature C4 and the curvature radius R4 at the insertion axis of the second curvature transition portion 13b in the maximum bent state may be derived from the following formula (4).

$$C4 = 1/R4 \approx (2 \tan \theta 4/2)/L4 \qquad (4)$$

The curvature C4 and the curvature radius R4 of the second curvature transition portion 13b in the maximum bent state are set to approximately 1/54 (1/mm) and approximately 54 mm, respectively.

The respective angles θ1 to θ4 and the respective distances L1 to L4 of the first bending portion 12a, the second bending portion 12b, the first curvature transition portion 13a and the second curvature transition portion 13b are set such that the respective curvature values at the insertion axes in the maximum bent state establish the relationship of C1>C2>C3>C4.

In other words, the respective angles θ1 to θ4 and the respective distances L1 to L4 of the first bending portion 12a, the second bending portion 12b, the first curvature transition portion 13a and the second curvature transition portion 13b are set such that the respective curvature radii at the insertion axes in the maximum bent state establish the relationship of R1<R2<R3<R4.

Accordingly, the insertion portion 6 of the endoscope 2 is configured to vary the curvature in the maximum bent state to be smaller stepwise from the first bending portion 12a to the second curvature transition portion 13b as shown in FIG. 9. In other words, the insertion portion 6 of the endoscope 2 is set to vary the curvature radius in the maximum bent state to be larger stepwise from the first bending portion 12a to the second curvature transition portion 13b as shown in FIG. 9. Referring to FIG. 10, the insertion portion 6 is set to vary each curvature radius of the respective portions 12a, 12b, 13a and 13b in the maximum bent state to be larger in four corresponding stages from the first bending portion 12a to the second curvature transition portion 13b.

In the embodiment, the curvature radius in the maximum bent state is varied to be larger consecutively in four stages, that is, from the first and the second bending portions 12a, 12b to the first and the second curvature transition portions 13a, 13b. However, the curvature radius in the maximum bent state may be varied to be larger in a plurality of stages, for example, two stages, six stages and the like.

Among the rotation ranges of the respective pieces 21 to 24, the rotation range of the first bending piece 21 at the most distal end side is set to the largest value, and the rotation range of the second curvature regulation piece 24 at the most proximal end side is set to the smallest value such that the curvature radius in the maximum bent state of the respective portions from the first bending portion 12a to the second curvature transition portion 13b is smoothly varied to gradually become larger. The insertion portion 6 of the endoscope 2 may be configured such that the curvature in the maximum bent state of the respective portions from the first bending portion 12a to the second curvature transition portion 13b is continuously varied to gradually become smaller.

The angle defined by the lines each formed by connecting the abutment portions Z (see FIG. 4) to the apex, that is, the common rotating axial center of the adjacent pieces such as the predetermined angles θ1 to θ4 and the length between the axes of the pivot members 42 such as L1 to L4 from the first bending portion 12a to the second curvature transition portion 13b may further be fractionized, respectively to become larger stepwise. The curvature in the maximum bending state may be continuously varied to become smaller from the first bending portion 12a to the second curvature transition portion 13b. The configuration for setting the curvature radius to become gradually larger from the first ending portion 12a to the second curvature transition portion 13b is not limited to the bending pieces 21, 22 and the curvature regulation pieces 23, 24.

The curvature transition portion 13 as the first flexible tube may be set to have its distal end portion bent with the predetermined force or lower, or with the curvature radius which is substantially the same as that of the bending portion 12 in the maximum bent state. The curvature transition portion 13 may be set to have its proximal end portion bent with the predetermined force or lower, or with the curvature radius which is substantially the same as that of the force quantity transmission portion 14 in the maximum bent state. Each curvature radius at the distal end and the proximal end of the curvature transition portion 13 in the embodiment to be described below may be set in the similar way.

The force quantity transmission portion 14 of the insertion portion 6 exhibits the flexural rigidity higher than those of the bending portion 12 and the curvature transition portion 13 as described above. In other words, the force quantity transmission portion 14 of the insertion portion 6 exhibits the flexibility lower than those of the bending portion 12 and the curvature transition portion 13.

Figure 12:
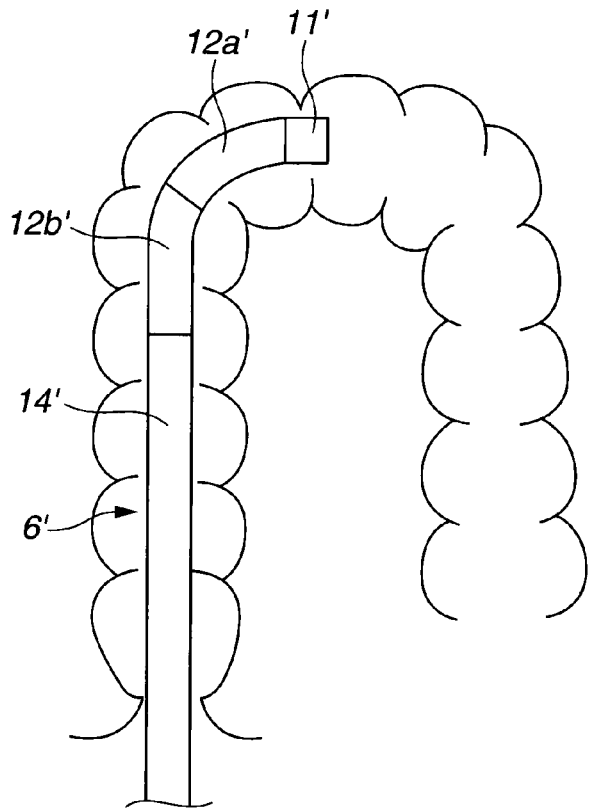
FIG. 12 is an explanatory view showing the state where the insertion portion of the generally employed endoscope is inserted into the large intestine.
Figure 13:
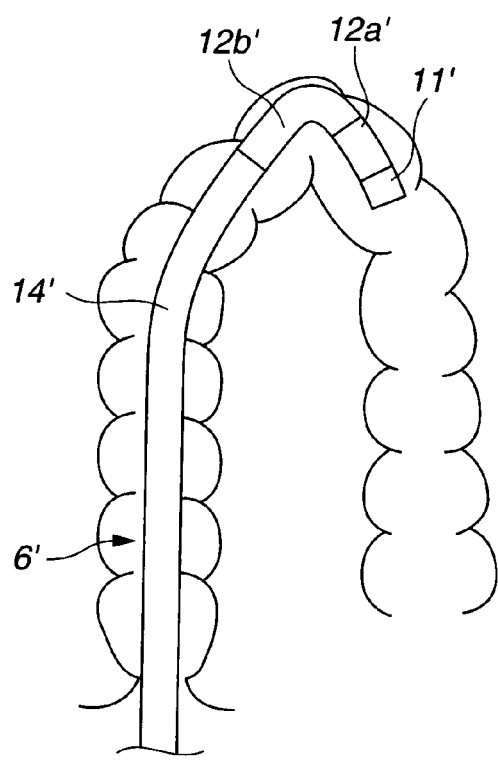
FIG. 13 is an explanatory view showing the state where the insertion portion of the generally employed endoscope is inserted into the large intestine.
Figure 14:
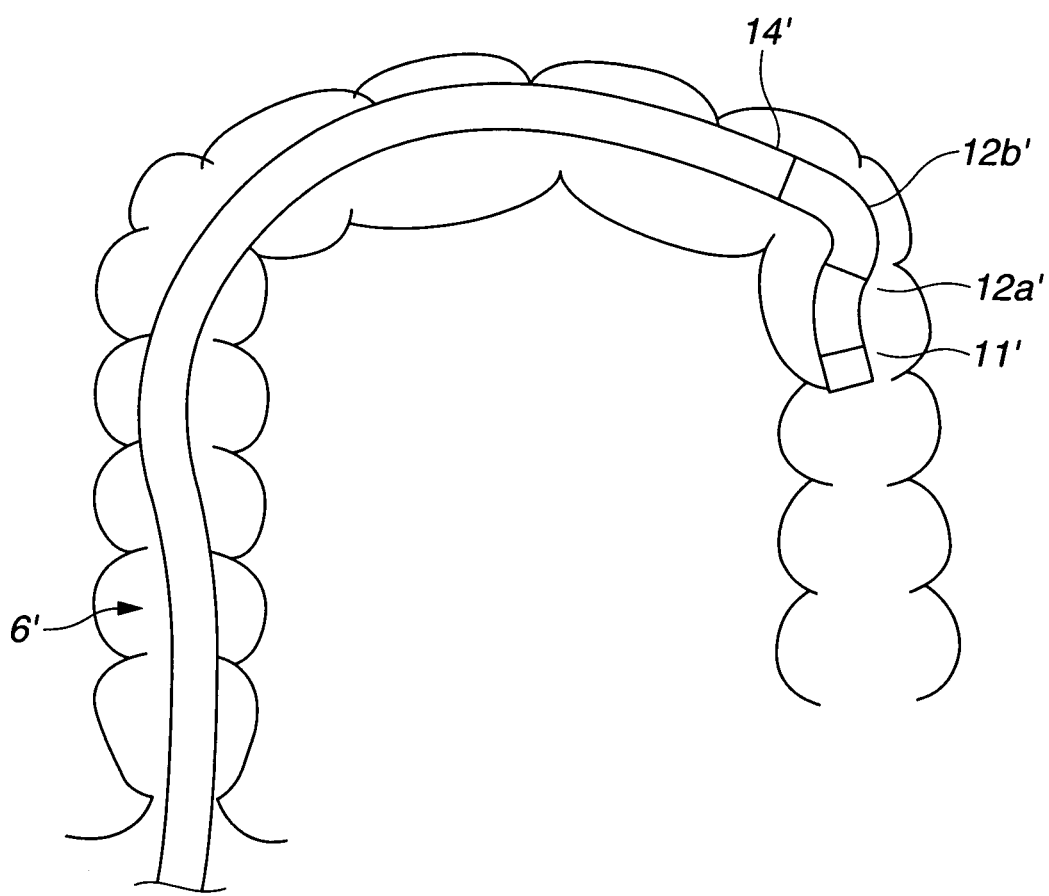
FIG. 14 is an explanatory view showing the state where the insertion portion of the generally employed endoscope is inserted into the large intestine.

Referring to FIGS. 12 to 14, the state where the insertion portion of the generally employed endoscope is inserted into the body cavity, for example, the large intestine will be described.

As described above, the generally employed endoscope (see Patent Documents 1 and 2) includes the second bending portion. The endoscope provided with no second bending portion has been widely used before introduction of the aforementioned endoscope.

The insertion portion of the endoscope provided with no second bending portion is formed of three portions, that is, the distal end configuration portion, the bending portion, and the flexible tube portion, for example. The bending portion exhibits elasticity allowed to positively bend. The flexible tube portion exhibits a predetermined rigidity for transmitting the pressing force applied by the operator to the distal end side.

The flexible tube portion has a longer length in the longitudinal direction, and a higher rigidity than those of the bending portion, respectively. When the insertion portion passes the flexed portion in the body cavity, only a part of the entire insertion axis, that is, the bending portion is locally flexed owing to the difference in the rigidity between the bending portion and the flexible tube portion. As the curvature radius at the insertion axis greatly varies, the problem of difficulty for the flexible tube portion to follow up the bending portion occurs.

It is difficult for the operator to allow the insertion portion to smoothly pass the flexed portion in the body cavity. The joint portion between the bending portion and the flexible tube portion is likely to be stuck with the flexed portion in the body cavity.

The insertion portion 6' of the generally employed endoscope as proposed in Patent Document 1 or 2 is formed of the distal end configuration portion 11', the first bending portion 12a', the second bending portion 12b', and the flexible tube portion 14' in the order from the distal end portion as shown in FIG. 12. The first bending portion 12a' of the generally employed endoscope exhibits the higher rigidity, that is, lower flexibility than that of the second bending portion 12b'.

First the operator inserts the insertion portion 6' of the generally employed endoscope from the distal end configuration portion 11' to the large intestine through the anus of the patient. At this time, the operator pushes the distal end portion of the insertion portion 6' to be inserted to the large intestine of the patient while grasping to twist the flexible tube portion 14' of the insertion portion 6'.

When the distal end configuration portion 11' reaches the flexed portion of the intestine, the operator bends the first bending portion 12a' to follow the flexed state of the intestine, and further pushes the flexible tube portion 14' grasped by the operator to the inside of the large intestine: At this time, the second bending portion 12b' exhibits higher flexibility than that of the first bending portion 12a', that is, easily deformable as shown in FIG. 13. The second bending portion is acutely bent as it abuts on the wall of the flexed portion of the intestine under the pushing force transmitted from the flexible tube portion 14' at the proximal end side.

The thus acutely bent second bending portion 12b' is stuck with the intestine wall to be pushed upward. When the operator further pushes the grasped flexible tube portion 14' deep into the large intestine in the state where the second bending portion 12b' pushes up the large intestine with respect to the flexed portion thereof, the intestine may be excessively stretched as shown in FIG. 14.

As a result, the patient suffers the pain. As the second bending portion 12b' receives the resistance in abutment on the flexed portion of the intestine, more time is required for the operator to insert the insertion portion 6' into the target site.

The function which occurs upon insertion of the insertion portion 6 of the thus configured endoscope 2 into the body cavity, the large intestine, for example, will be described referring to FIGS. 15 to 17.

The operator inserts the insertion portion 6 of the endoscope 2 according to the embodiment from the distal end configuration portion 11 to the large intestine through the anus of the patient while grasping to twist the force quantity transmission portion 14 so as to be pushed in the same way as in the case of the generally employed endoscope. At this time, the force quantity transmission portion 14 exhibits the predetermined rigidity sufficient to transmit the pressing force applied from the operator to the distal end portion of the insertion portion 6, that is, the bending portion 12 and the curvature transition portion 13.

Figure 15:
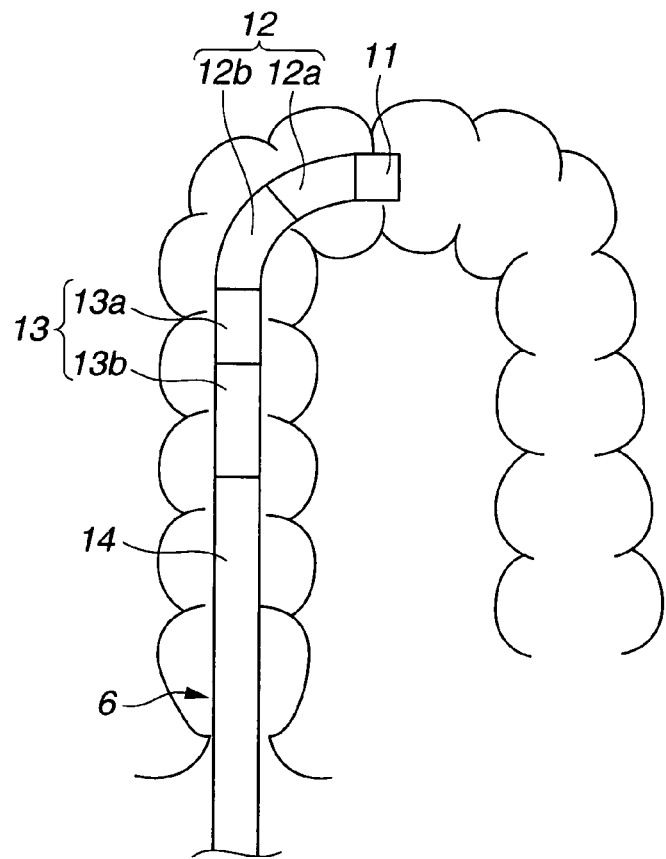
FIG. 15 is an explanatory view showing the state where the insertion portion of the endoscope according to the first embodiment shown in FIG. 1 is inserted into the large intestine.

Referring to FIG. 15, the insertion portion 6 of the endoscope 2 which has reached the flexed portion within the large intestine has the bending portion 12 operated to be bent such that the distal end configuration portion 11 is directed to the desired insertion direction, that is, the direction along the flexed portion of the large intestine. Specifically, based on the endoscopic image displayed on the monitor 5, the operator performs the predetermined operation of the bending operation knob 7b of the operation portion 7 in the endoscope 2 so as to bend the first bending portion 12a and the second bending portion 12b as components of the bending portion 12 in the direction along the flexed portion of the large intestine.

When the operator further pushes the force quantity transmission portion 14 grasped thereby deep into the large intestine, the bending portion 12 is pushed against the intestine wall and brought into the maximum bent state.

As the first bending portion 12a and the second bending portion 12b have different curvature radii R1 and R2 at the insertion axes, respectively, the curvature of the bending portion 12 in the maximum bent state varies stepwise. The second bending portion 12b is bent stepwise more gently than the first bending portion 12a in the maximum bent state of the bending portion 12.

Figure 16:
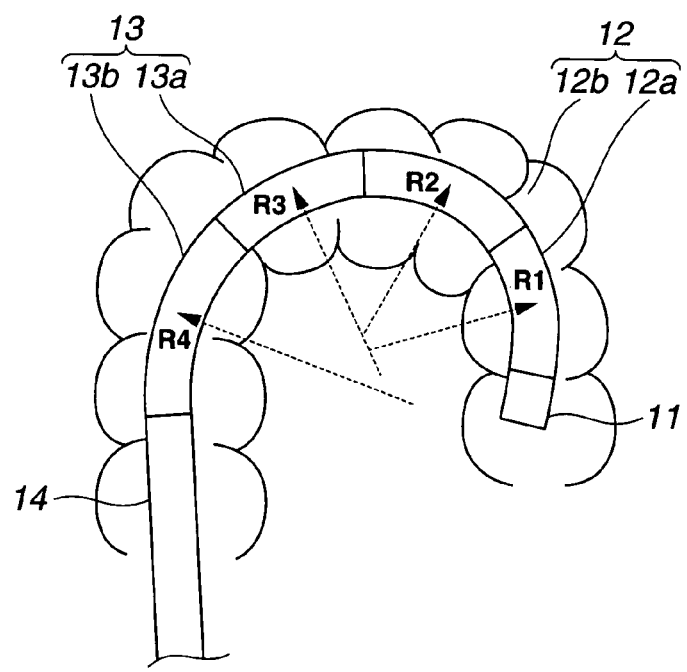
FIG. 16 is an explanatory view showing the state where the insertion portion of the endoscope according to the first embodiment shown in FIG. 1 is inserted into the large intestine.
Figure 17:
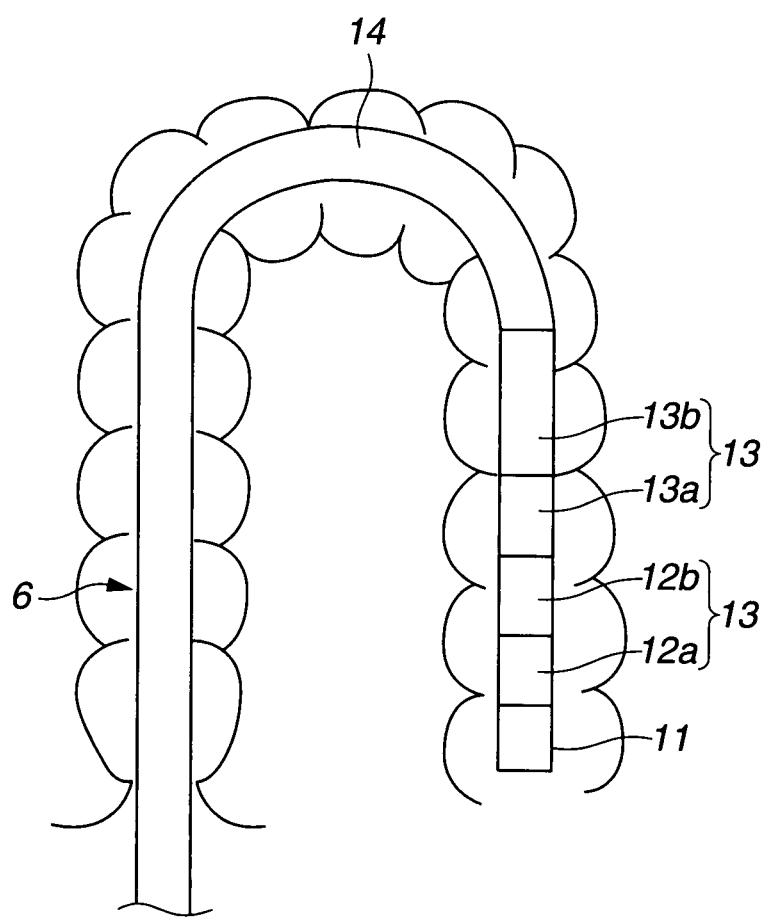
FIG. 17 is an explanatory view showing the state where the insertion portion of the endoscope according to the first embodiment shown in FIG. 1 is inserted into the large intestine.

Referring to FIG. 16, the curvature transition portion 13 is bent along the flexed portion of the intestine by following up the bending portion 12. In this case, when the force quantity transmission portion 14 grasped by the operator is further pushed deep into the large intestine, the curvature transition portion 13 is pushed against the intestine wall to be brought into the maximum bent state.

As the curvature of the curvature transition portion 13 at the insertion axis is held smaller than that of the bending portion 12, the curvature transition portion is allowed to pass the flexed portion of the intestine smoothly without being brought into the acute bending state. That is, the curvature of the first curvature transition portion 13a in the maximum bent state becomes smaller than that of the second bending portion 12b of the bending portion 12 so as to regulate the bending with the larger curvature radius R3.

The curvature of the second curvature transition portion 13b in the maximum bent state at the insertion axis is set to be smaller than that of the first curvature transition portion 13a so as to regulate the bending with the larger curvature radius R4.

After the bending portion 12 passes the flexed portion of the intestine, the operator further pushes the grasped force quantity transmission portion 14 deep into the large intestine while adjusting the bending state of the bending portion 12 to the linear state or the flexed state of the intestine. After the curvature transition portion 13 passes the flexed portion of the intestine, the force quantity transmission portion 14 receives the abutment force from the intestine wall to follow up the curvature transition portion 13 to pass the flexed portion of the intestine smoothly while smoothly bending as shown in FIG. 17. The force for pushing the insertion portion 6 deep into the large intestine applied by the operator may be approximately 2 Kg to maximum.

The endoscope 2 according to the embodiment is configured to gently decrease the value of the curvature in the maximum bent state from the first bending portion 12a to the second curvature transition portion 13b, resulting in the gentle change in the curvature. This makes it possible to easily insert the bending portion 12 and the curvature transition portion 13 deep into the large intestine as the body cavity while passing the flexed portion of the intestine smoothly without being brought into the acute bent state.

The resistance generated when the bending portion 12 passes the flexed portion of the intestine may be suppressed. This makes it possible to reduce the burden and the pain suffered by the patient who receives the endoscopic inspection using the endoscope 2 according to the embodiment.

The values of each curvature of the first bending portion 12a, the second bending portion 12b, the first curvature transition portion 13a and the second curvature transition portion 13b in the maximum bent states, respectively of the thus configured endoscope 2 are set to satisfy the relationship of C1>C2>C3>C4. That is, the values of each minimum curvature radius of the aforementioned portions are set to satisfy the relationship of R1<R2<R3<R4. This makes it possible to reduce the insertion force for allowing the distal end portion of the insertion portion 6 to pass the flexed portion of the intestine by approximately 30 to 40% compared with the generally employed endoscope.

Accordingly, the endoscope 2 of the embodiment considerably improves the operability for inserting the insertion portion 6 into the flexed body cavity.

Second Embodiment

A second embodiment according to the present invention will be described referring to the drawings.

Figure 18:
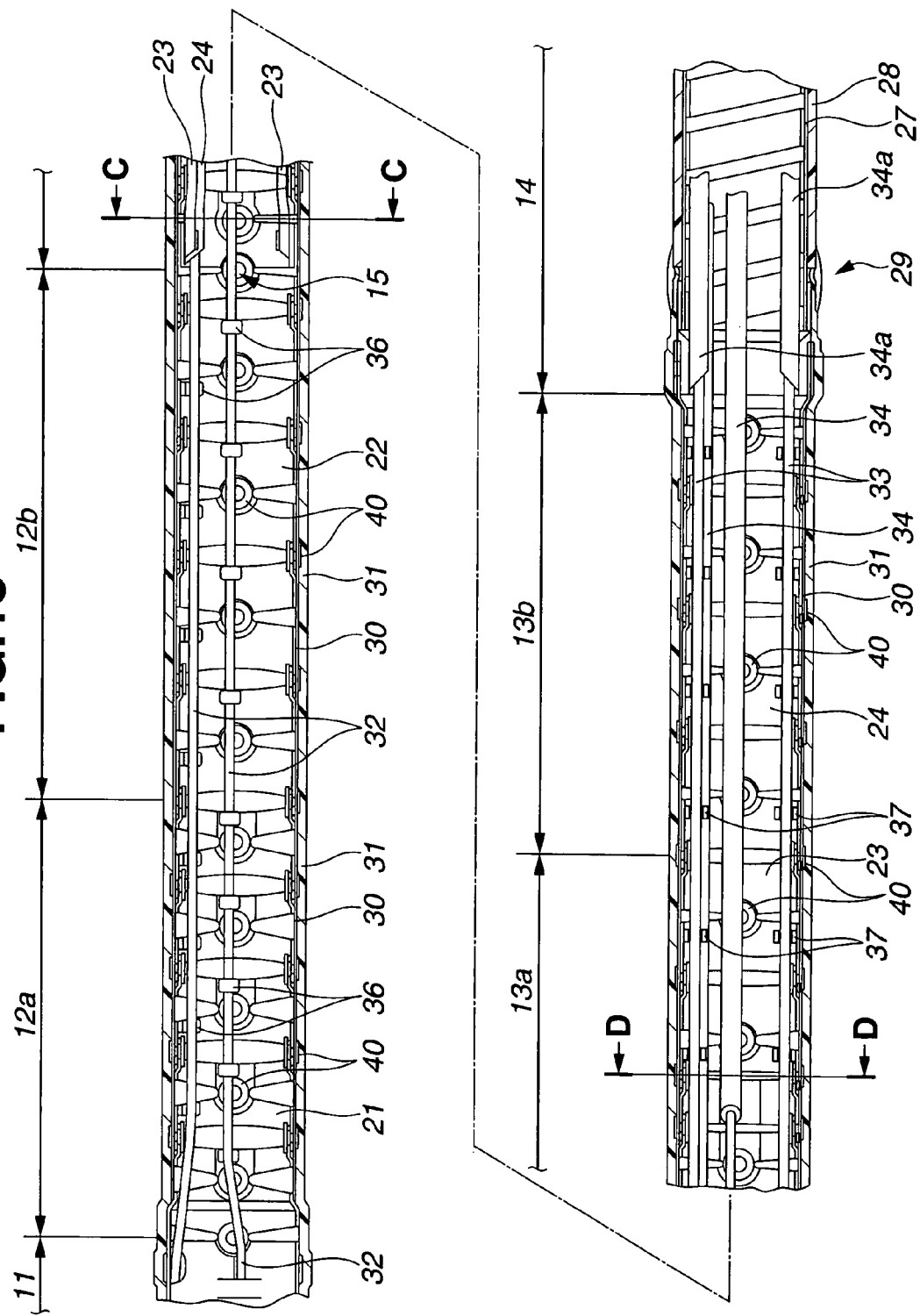
FIG. 18 is a sectional view showing a section of the distal end portion of the insertion portion of the endoscope according to a second embodiment, which has been cut in the longitudinal direction.
Figure 19:
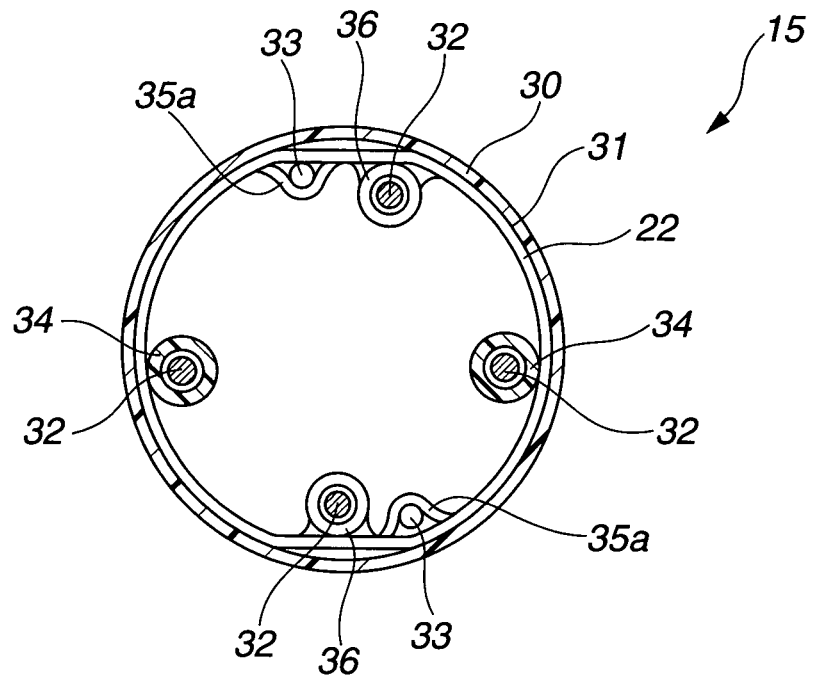
FIG. 19 is a sectional view of the insertion portion taken along line C-C shown in FIG. 18.
Figure 20:
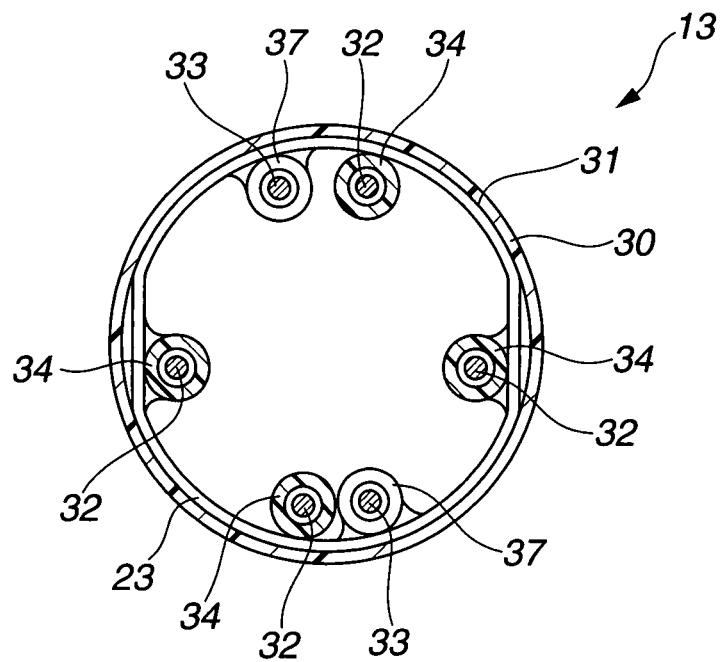
FIG. 20 is a sectional view of the first curvature transition portion of the insertion portion taken along line D-D shown in FIG. 18.

FIG. 18 is a sectional view showing the section of the distal end portion of the insertion portion 6, which has been cut in the longitudinal direction. FIG. 19 is a sectional view of the insertion portion taken along line C-C shown in FIG. 18. FIG. 20 is a sectional view of the first curvature transition portion of the insertion portion taken along line D-D shown in FIG. 18. In the embodiment, the configuration, functions and effects of the endoscope which are the same as those of the endoscope that has been already described in the first embodiment will be designated with the same codes, and the explanations thereof, thus, will be omitted. The explanation with respect only to the different configuration, functions and the effects will be made hereinafter.

Referring to FIG. 18, besides the four bending operation wires 32 for bending operation of the bending portion 12 as described in the first embodiment, two curvature transition operation wires 33 are inserted into the insertion portion 6 of the embodiment such that the first curvature transition portion 13a and the second curvature transition portion 13b of the curvature transition portion 13 are pulled and loosened from the distal end side.

The curvature transition operation wires 33 are inserted and held in the wire guide 37 in the curvature transition portion 13 to be described later, and inserted into the coil sheath 34a from the force quantity transmission portion 14 to the distal end, respectively. Referring to FIG. 19, each distal end portion of the curvature transition operation wires 33 is held and fixed at two points arranged in substantially vertical direction shown in FIG. 19 in the first curvature regulation piece 13a at the most distal end side.

Likewise the bending operation wires 32, those curvature transition operation wires 33 are linked with a not shown bending operation mechanism having the proximal end portion disposed in the operation portion 7 (see FIG. 1) so as to be pulled or loosened alternately. The bending operation mechanism is linked to a not shown curvature transition operation knob provided on the operation portion 7.

Accordingly, those curvature transition operation wires 33 are pulled and loosened through the predetermined operation of the not shown curvature transition portion operation knob. As the curvature transition operation wires 33 are pulled and loosened, the curvature transition portion 13 is operated to be bent in two directions, that is, up and down.

Referring to FIG. 20, two wire guides 37 through which the curvature transition operation wires 33 are inserted and held at every one piece are fixed onto the inner peripheral surface around the proximal end surfaces of the first and the second curvature regulation pieces 23, 24 in the curvature transition portion 13 through such means as welding. Those two wire guides 36 are provided on the inner peripheral surface at positions each displaced in the direction around the insertion axis at 180° which divides the circumference of each of the curvature regulation pieces 23, 24 into two equivalent parts, or at the positions around the insertion axis with respect to the pair of the joint portions 40 each displaced at 90°.

The operator who uses the endoscope 2 according to the embodiment is allowed to operate to bend only the curvature transition portion 13 in the desired two up and down directions with no need of pushing the curvature transition portion 13 against the intestine wall to be bent until respective curvatures (maximum curvature radii R3, R4) in the maximum bending state of respective portions when the first curvature transition portion 13a and the second curvature transition portion 13b of the curvature transition portion 13 pass the flexed portion of the intestine such as the large intestine as the body cavity.

As a result, in addition to the effect derived from the first embodiment, the distal end portion of the insertion portion 6, especially, the curvature transition portion 13 passes the flexed portion of the body cavity further smoothly.

The four curvature transition operation wires may be used such that the first and the second curvature transition portions 13a and 13b of the curvature transition portion 13 are operated to be bent in the lateral direction, that is, left and right directions.

Third Embodiment

A third embodiment according to the present invention will be described referring to the drawings.

Figure 21:
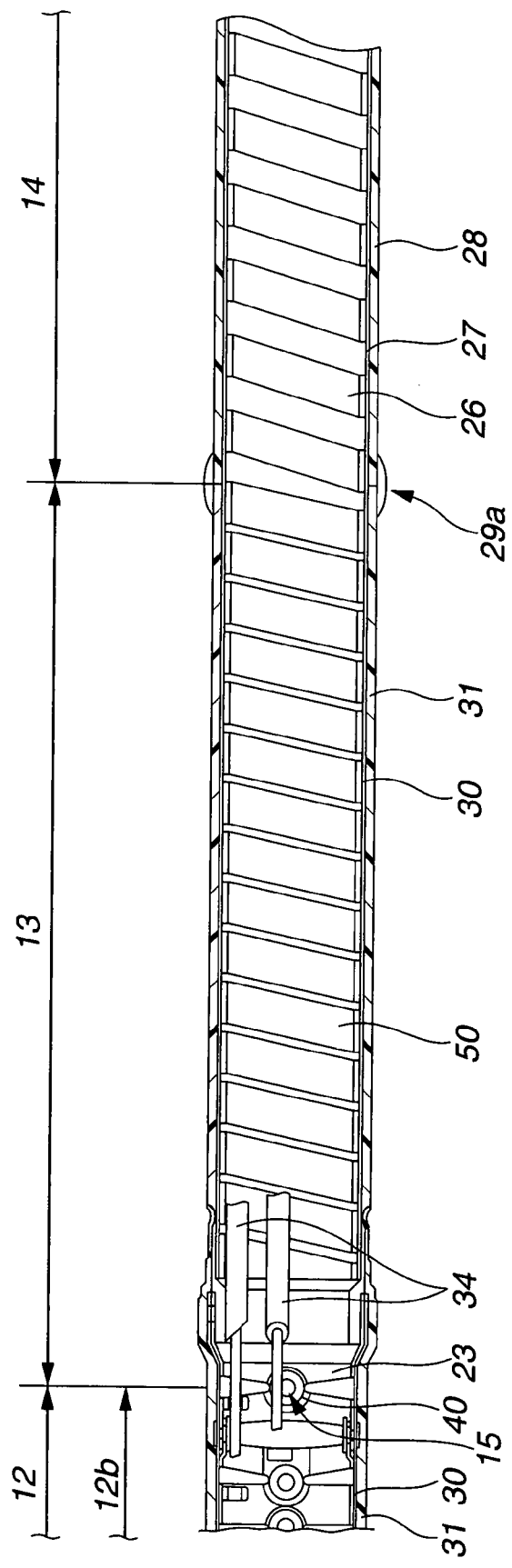
FIG. 21 is a sectional view showing a section of the distal end portion of the insertion portion of the endoscope according to a third embodiment, which has been cut in the longitudinal direction.
Figure 22:
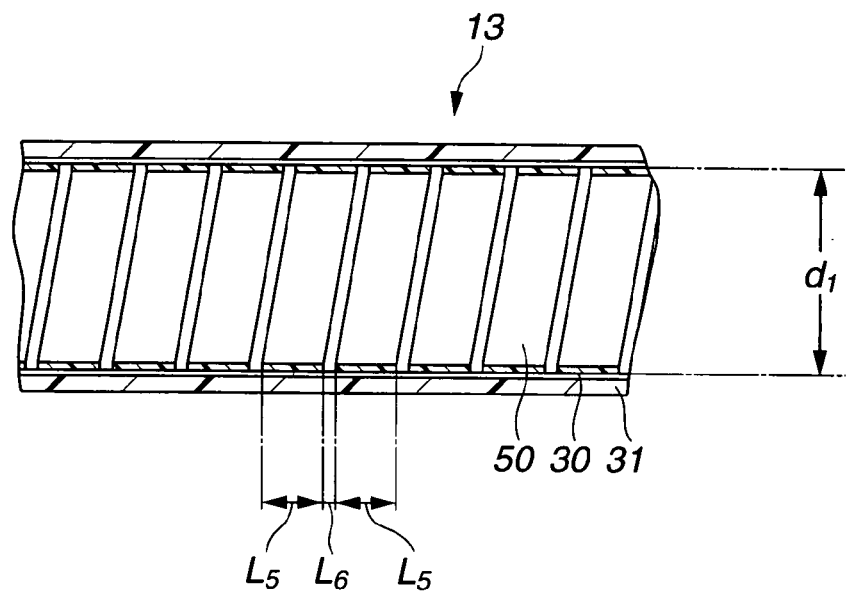
FIG. 22 is a sectional view showing a section of the curvature transition portion of the insertion portion shown in FIG. 21 with the linear insertion axis, which has been cut in the longitudinal direction.
Figure 23:
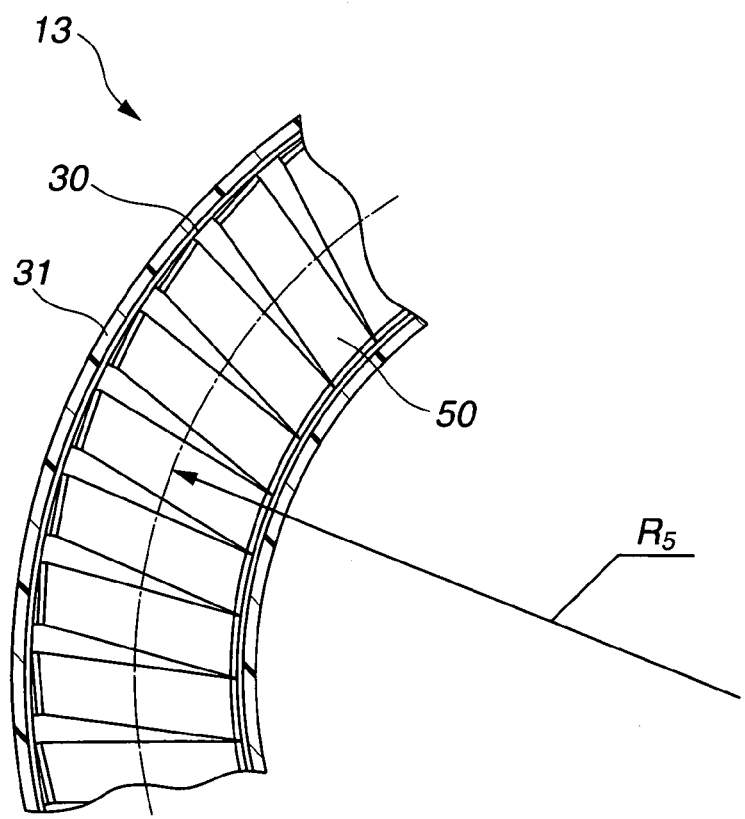
FIG. 23 is a sectional view showing a section of the curvature transition portion of the insertion portion in the maximum bent state shown in FIG. 21, which has been cut in the longitudinal direction.

FIG. 21 is a sectional view showing the section of the distal end portion of the insertion portion 6, which has been cut in the longitudinal direction. FIG. 22 is a sectional view of the curvature transition portion in substantially the linear state, which has been cut in the longitudinal direction. FIG. 23 is a sectional view of the curvature transition portion in the maximum bent state, which has been cut in the longitudinal direction.

In the description of the embodiment, the configuration, functions and effects which are the same as those described in the first and the second embodiments will be designated as the same codes, and explanation thereof, thus, will be omitted. The different configuration, functions and effects will only be described hereinafter.

Referring to FIG. 21, a curvature regulation tube 50 as a flex tube where the belt-like member is helically formed with a gap is inserted into the curvature transition portion 13 in place of the curvature regulation piece. The curvature regulation tube 50 in the curvature transition portion 13 may be formed of a single layer, or a plurality of layers including double-layer, triple-layer and the like.

The outer circumference of the curvature regulation tube 50 in the curvature transition portion 13 is covered with the bending braid 30 which has its outer circumference further covered with the outer coat 31 as a first outer tube (first outer member) likewise the first and the second embodiments. The distal end portion of the curvature regulation tube 50 at the boundary between the second bending portion 12b and the first curvature transition portion 13a is connected to the second bending piece 22.

The force quantity transmission portion 14 is covered with the outer coat 28. The joint portion between the curvature transition portion 13 and the force quantity transmission portion 14 is provided with a reel adhesion portion 29a which adheres the outer coat 31 of the curvature transition portion 13 and the outer coat 28 of the force quantity transmission portion 14 with the reel.

In the embodiment, the curvature transition portion 13 is formed of a single part, but may be formed of two parts including the first curvature transition portion at the distal end side and the second curvature transition portion at the proximal end side likewise the first and the second embodiments.

Referring to FIG. 22, the section of the curvature regulation tube 50 which is cut in the direction where the helically formed belt-like member is in parallel with the insertion axis of the curvature transition portion 13 in the linear state has the longitudinal length set to a predetermined value L5. The distance of the gap between the sections is set to a predetermined value L6. The external circumferential diameter of the curvature regulation tube 50 is set to a predetermined value d1.

Referring to FIG. 23, the curvature transition portion 13 is brought into the maximum bent state when there is no gap in the bending direction formed by the belt-like member of the curvature regulation tube 50, and the side surfaces of the belt-like member are in the abutment state inside the bending portion. More specifically, the curvature transition portion 13 is brought into the maximum bent state when the side surface of the belt-like member inside the insertion axis which forms the arc through the bending is in the abutment state so as to prevent the bending of the curvature transition portion 13.

The curvature transition portion 13 has the curvature C5 and the curvature radius R5 in the maximum bending state which are set based on the relationship among the predetermined longitudinal length L5 of the section surface cut in the direction where the belt-like member of the curvature regulation tube 50 is in parallel with the insertion axis, a predetermined length L6 of the gap between the section surfaces, and the external diameter d1 of the curvature regulation tube 50 when the insertion axis is in the linear state.

The curvature C5 and the curvature radius R5 of the curvature transition portion 13 in the maximum bent state may be calculated using the following formula (5).

$$C5 = 1/R5 \approx 2 \times L6/(L5+L6) \times d1 \quad (5)$$

The curvature transition portion 13 according to the embodiment has the predetermined values of the length L5, L6 and the external diameter d1 of the curvature regulation tube 50 which are set such that curvature C5 in the maximum bending state (maximum curvature radius R5) and the curvatures C1, C2 (minimum curvature radii R1, R2) of the first bending portion 12a and the second bending portion 12b described in the first embodiment at the insertion axes in the maximum bending state satisfy the relationship of C1>C2>C5 (R1<R2<R5).

In the case where the curvature transition portion 13 is formed of two portions, the curvature of the second curvature transition portion at the proximal end side in the maximum bent state is set to be smaller than the curvature of the first curvature transition portion at the distal end side in the maximum bent state. That is, the curvature radius of the second curvature transition portion at the proximal end side in the maximum bent state is set to be larger than the curvature radius of the first curvature transition portion at the distal end side in the maximum bent state.

In the case where the curvature regulation tube 50 formed of a plurality of layers, for example, double-layer or triple-layer are provided in the curvature transition portion 13, the length and the curvature radius of one of the layers of the curvature regulation tube 50 may be set as described below. The curvature C5 and the curvature radius R5 in the maximum bent state may be set based on the relationship among the predetermined longitudinal length L5 of the section surface which is cut in the direction where the belt-like member of the curvature regulation tube 50 is in parallel with the insertion axis of the curvature transition portion 13 in the linear state, the predetermined length L6 of the gap between the section surfaces, and the external diameter d1 of the curvature regulation tube 50.

As the curvature regulation tube 50 in the curvature transition portion 13 has the flex structure where the belt-like member is helically formed, the same regulation radius may be obtained in the arbitral bending direction at 360° around the insertion axis. The curvature transition portion 13 of the endoscope 2 according to the embodiment exhibits excellent twisting follow-up performance, operability and smooth insertion in addition to the effects derived from the first and the second embodiments.

Figure 24:
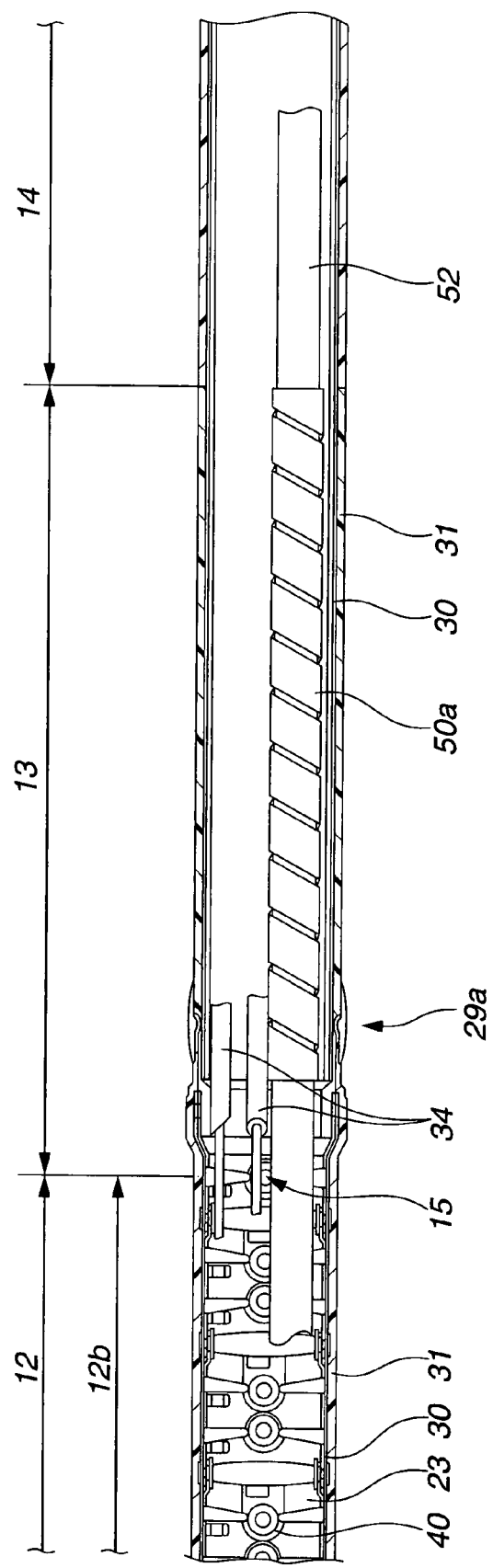
FIG. 24 is a sectional view showing a section of the distal end portion of the insertion portion of the endoscope which has been cut in the longitudinal direction for explaining the curvature regulation tube externally fit with a forceps channel of the insertion portion shown in FIG. 21.

Referring to FIG. 24, a curvature regulation tube 50a may have its outer circumference covered over the range of the curvature transition portion 13 in which the forceps channel 52 is inserted into the insertion portion 6. The forceps channel 52 is a tube which has the opening 11c (see FIG. 2) formed in the distal end surface of the distal end configuration portion 11, through which the treatment instrument such as the forceps is inserted. As the curvature regulation tube 50a has the same configuration as that of the aforementioned curvature regulation tube 50, the detailed explanation thereof will be omitted.

Besides the forceps channel 52, the curvature regulation tube 50a may have members to be inserted into the insertion portion 6 of the endoscope 2, for example, the communication cable, the light guide fiber, the air/water feed tube, and the coil sheath covered over the range of the curvature transition portion 13.

Fourth Embodiment

A fourth embodiment according to the present invention will be described referring to the drawings.

Figure 25:
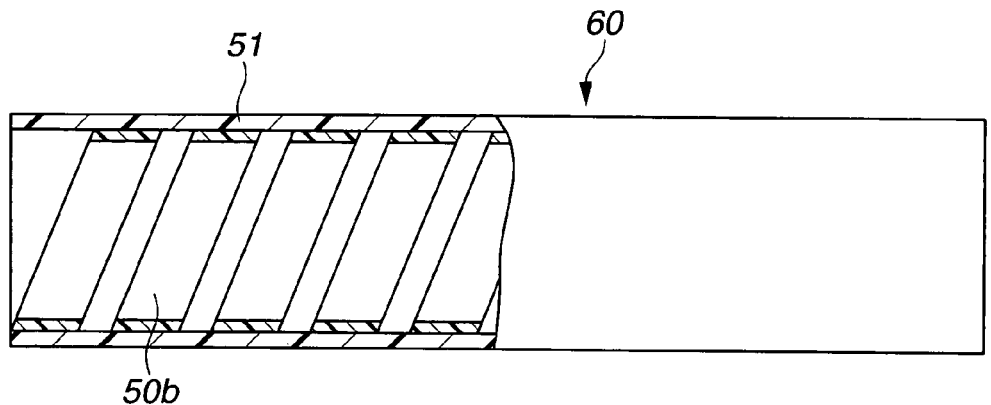
FIG. 25 is a partially sectional view representing a configuration of the curvature regulation body according to a fourth embodiment.
Figure 26:
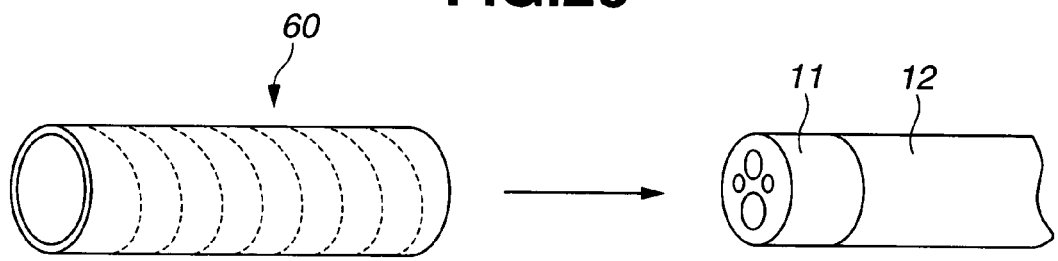
FIG. 26 is an explanatory view representing the state before the curvature regulation body shown in FIG. 25 is externally fit with the insertion portion of the endoscope.
Figure 27:
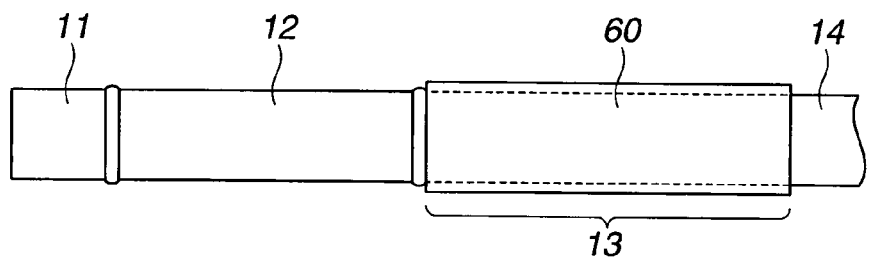
FIG. 27 is a side view of the insertion portion of the endoscope in the state where the curvature regulation body is externally attached to the flexible tube portion of the insertion portion shown in FIG. 26.
Figure 28:
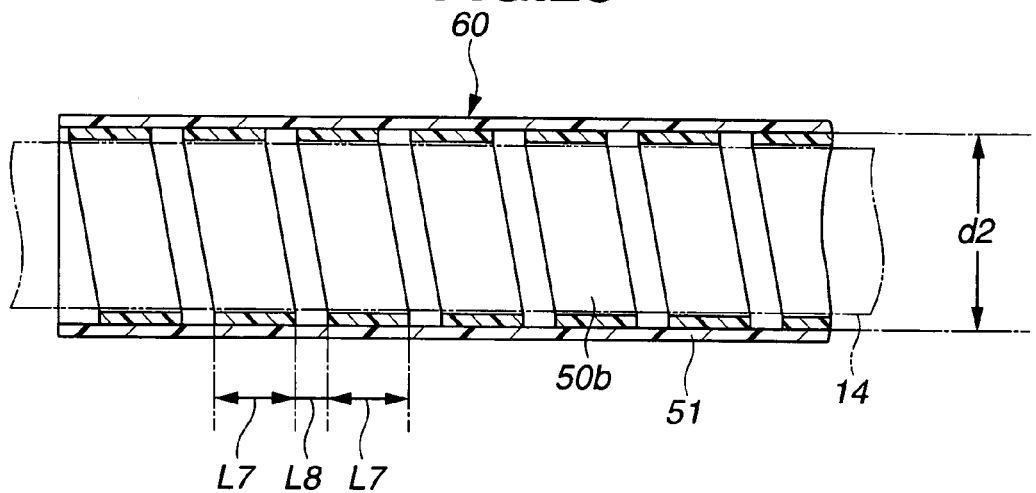
FIG. 28 is a sectional view showing a section of the curvature regulation body of the insertion portion with the linear insertion axis shown in FIG. 26, which has been cut in the longitudinal direction.
Figure 29:
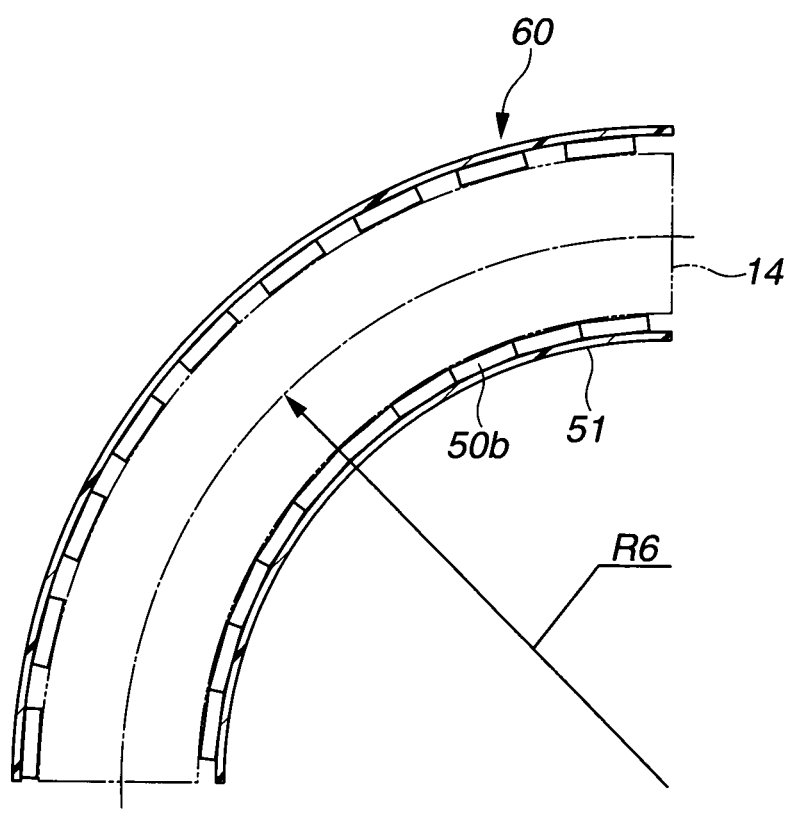
FIG. 29 is a sectional view showing the section of the curvature regulation body in the state where the insertion portion shown in FIG. 26 is brought into the maximum bent state, which has been cut in the longitudinal direction.

FIG. 25 is a partially sectional view showing the configuration of the curvature regulation body. FIG. 26 is an explanatory view showing the state before the curvature regulation body is externally fit with the insertion portion of the endoscope. FIG. 27 is a sectional view of the insertion portion of the endoscope in the state where the curvature regulation body is externally fit with the flexible tube portion of the insertion portion. FIG. 28 is a sectional view showing the section of the curvature regulation body with the insertion axis in the linear state which has been cut in the longitudinal direction. FIG. 29 is a sectional view showing the section of the curvature regulation body in the maximum bent state which has been cut in the longitudinal direction. In the embodiment, the configuration, functions, effects of the endoscope which are the same as those described in the previous embodiments are designated with the same codes, and the explanations thereof, thus, will be omitted. The different configuration, functions and effects will only be described hereinafter.

Referring to FIGS. 25 to 27, the force quantity transmission portion 14 may be partially formed to be the curvature transition portion 13 by the use of a substantially cylindrical curvature regulation body 60 which is detachable with respect to the insertion portion 6 of the endoscope 2. Specifically, the curvature regulation body 60 is formed of a curvature regulation tube 50$b$, and an outer coat 51 which covers the outer circumference of the curvature regulation tube 50$b$, and has the inner diameter which is substantially the same to or slightly smaller than the external diameter of the insertion portion 6 of the endoscope 2. Likewise the curvature regulation tube 50 as described in the third embodiment, the curvature regulation tube 50$b$ is the flex tube where the belt-like member is helically formed with the gap.

Referring to FIG. 26, the curvature regulation body 60 receives insertion of the insertion portion 6 from the distal end configuration portion 11 of the endoscope 2. Referring to FIG. 27, the curvature regulation body 60 covers a part of the force quantity transmission portion 14 so as to have the distal end positioned at the most distal end of the force quantity transmission portion 14, that is, the most proximal end of the bending portion 12. The curvature transition portion 13 is formed on the force quantity transmission portion 14 which is covered with the curvature regulation body 60.

The curvature and the maximum curvature radius at the insertion axis of the curvature transition portion 13 formed by the curvature regulation body 60 in the maximum bent state are set in the same manner as in the case of the curvature regulation tube 50 in the third embodiment. That is, the longitudinal length of the section surface of the curvature regulation tube 50$b$ cut in the direction where the helically formed belt-like member is in parallel with the insertion axis is set to a predetermined value of L7. The distance of the gap between the section surfaces is set to the predetermined value of L8. The external circumferential diameter of the curvature regulation tube 50$b$ is set to the predetermined value of d2.

Referring to FIG. 29, the curvature regulation body 60 is brought into the maximum bent state when the side surfaces of the belt-like members inside the insertion axis which forms the arc through bending are in the abutment state to prevent the bending operation.

The curvature regulation body 60 has the curvature C6 and the curvature radius R6 in the maximum bent state which are set in accordance with the relationship among the predetermined longitudinal length L7 of the section surface which is cut in the direction where the belt-like member of the curvature regulation tube 50$b$ is in parallel with the insertion axis in the linear state, the predetermined length L8 of the gap formed between the section surfaces, and the external diameter d2 of the curvature regulation tube 50$b$.

The curvature C6 and the curvature radius R6 of the curvature regulation body 60 in the maximum bent state may be calculated using the following formula (6).

$$C6=1/R6\approx 2\times L8/(L7+L8)\times d2 \quad (6)$$

The curvature regulation body 60 sets the predetermined values of the length L7, length 8 and the predetermined external diameter d2 of the curvature regulation tube 50$b$ such that the curvature C6 in the maximum bent state becomes smaller than the curvature of the bending portion 12 in the maximum bent state. That is, the curvature regulation body 60 sets the predetermined values of the length L7, the length L8 and the predetermined external diameter d2 of the curvature regulation tube 50$b$ such that the curvature radius R6 in the maximum bent state becomes larger than the curvature radius of the bent portion 12 in the maximum bent state.

The force quantity transmission portion 14 covered with the curvature regulation body 60, that is, the curvature transition portion 13 in the present embodiment has the curvature and the minimum curvature radius in the maximum bent state equivalent to the curvature C6 and the curvature radius R6 of the curvature regulation body 60 in the maximum bent state.

As a result, according to the embodiment, as the curvature regulation body 60 is detachable with respect to the insertion portion 6 of the endoscope 2, the curvature regulation body 60 which has the curvature C6 (curvature radius R6) at the insertion axis set in accordance with the flexed state of the intestine as the body cavity of the patient may be used.

The curvature regulation body 60 may be of the disposable type or the reuse type.

Fifth Embodiment

A fifth embodiment according to the present invention will be described referring to the drawings.

Figure 30:
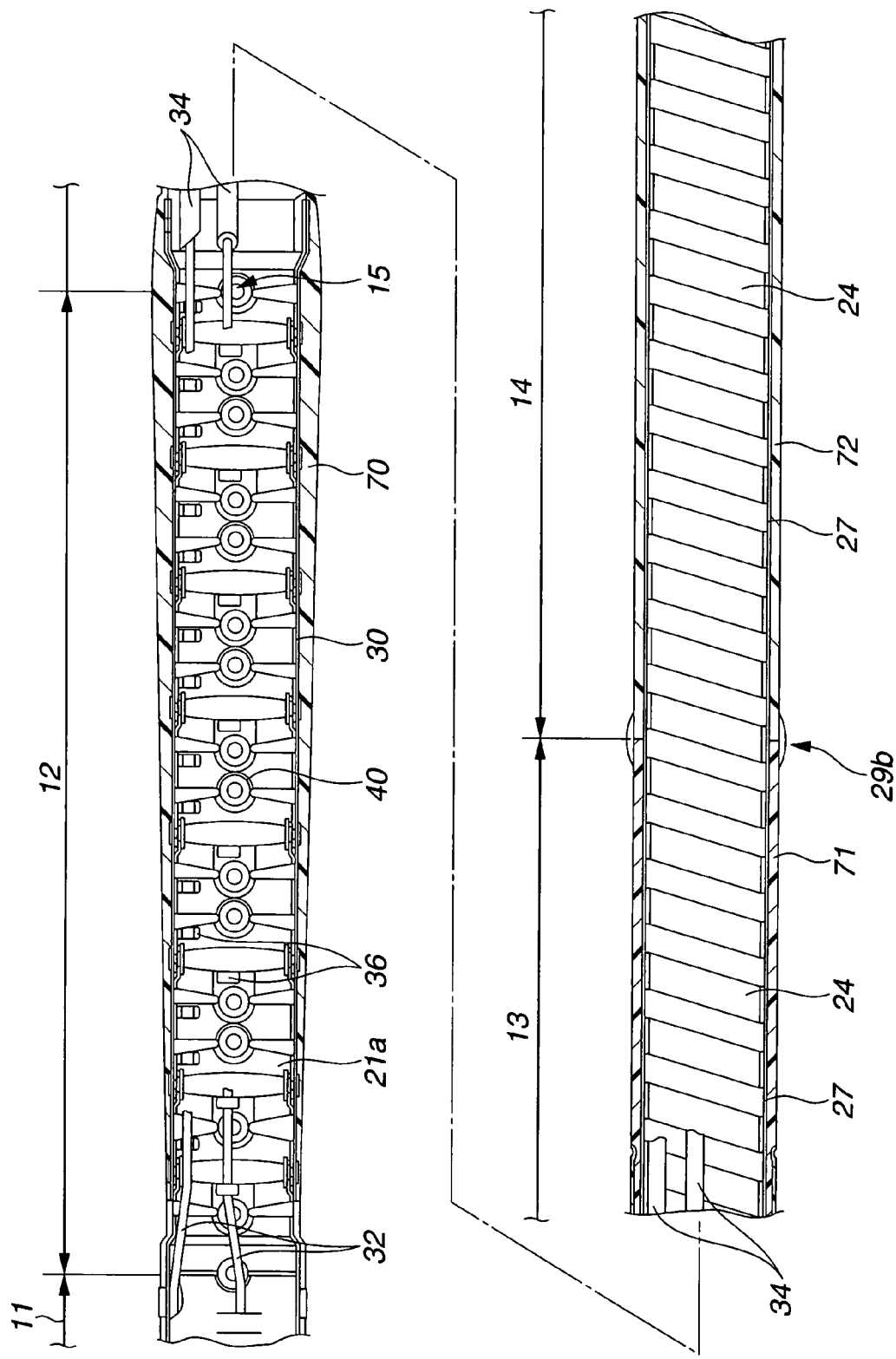
FIG. 30 is a sectional view showing the section of the distal end portion of the insertion portion of the endoscope according to a fifth embodiment, which has been cut in the longitudinal direction.

FIG. 30 is a sectional view showing the section of the distal end portion of the insertion portion according to the embodiment, which has been cut in the longitudinal direction. In the embodiment, the configuration, functions, and effects of the endoscope which are the same as those of the endoscope described in the previous embodiments will be designated with the same codes and explanation thereof, thus, will be omitted. The different configuration, functions and effects will only be described hereinafter.

Referring to FIG. 30, the insertion portion of the endoscope 2 according to the embodiment is formed of the distal end configuration portion 11, the bending portion 12, the curvature regulation portion 13 and the force quantity transmission portion 14 in the order from the distal end side.

The bending portion 12 is formed of a plurality of bending pieces 21$a$ which are rotatably connected in series. Those plural bending pieces 21a are covered with the bending braid 30 which is further covered with an outer coat 70 as a first outer insertion tube such that the bending portion 12 is formed. The thickness of the outer coat 70 of the bending portion 12 is gradually increased from the distal end side to the proximal end side. The rigidity of the outer coat 70, thus, gradually increases from the distal end side to the proximal end side, and accordingly, the flexural rigidity of the bending portion 12 gradually increases from the distal end side to the proximal end side.

The flex tube 26 as the helical tube is inserted into the curvature transition portion 13 and the force quantity transmission portion 14. The outer circumference of the flex tube 26 is covered with the braid 27 likewise the bending portion 12.

An outer coat 71 serving as a second outer tube is applied to the outer circumference of the braid 27 to cover the range of the curvature transition portion 13. An outer coat 72 serving as a third outer tube is applied to the outer circumference of the braid 27 to cover the range of the force quantity transmission portion 14.

The outer coat 71 of the curvature transition portion 13 and the outer coat 72 of the force quantity transmission portion 14 are formed of a synthetic resin with a predetermined rigidity formed by mixing a soft resin material, for example, polyurethane, and a rigid resin such as polyester.

The content of the soft resin contained in the outer coat 71 of the curvature transition portion 13 becomes high as it gets closer to the distal end side, and becomes low as it gets closer to the proximal end side, which is formed of the synthetic resin material with the higher content of the rigid resin. As the rigidity of the outer coat 70 becomes gradually high from the distal end side to the proximal end side, the flexural rigidity of the curvature transition portion 13 is set to be gradually increased from the distal end side to the proximal end side.

The distal end side of the outer coat 71 contains the mixture of the soft resin and the rigid resin at the predetermined compound ratio such that the flexural rigidity of the curvature transition portion 13 at the distal end side becomes substantially the same as that of the bending portion 12 at the proximal end side. The outer coats 71 and 72 are linked at the joint portion between the curvature transition portion 13 and the force quantity transmission portion 14 with the reel adhesion portion 29*b*.

The outer coat 72 of the force quantity transmission portion 14 is formed of the synthetic resin through mixture of the soft resin and the rigid resin at constant compound ratio over the whole length. The outer coat 72 contains the mixture of the soft resin and the rigid resin at the predetermined compound ratio such that the flexural rigidity of the force quantity transmission portion 14 becomes substantially the same as that of the curvature transition portion 13 at the proximal end side.

Figure 31:
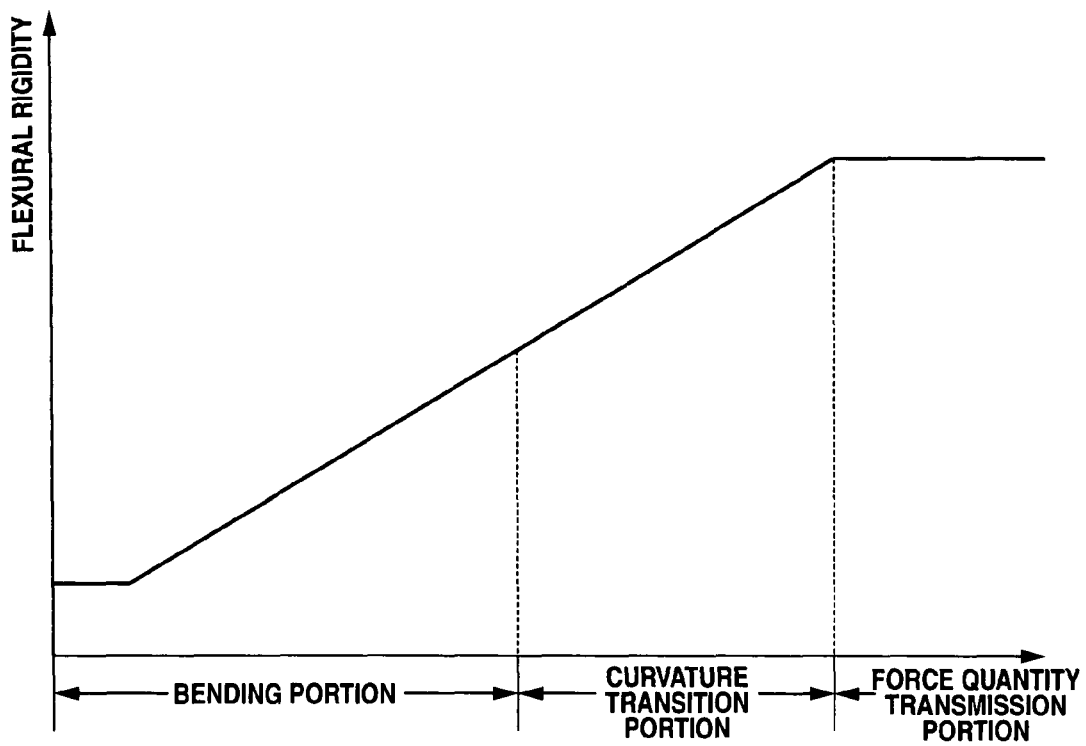
FIG. 31 is a graph representing each change in the flexural rigidity of the bending portion, the curvature transition portion and the flexible tube portion of the insertion portion shown in FIG. 30.
Figure 32:
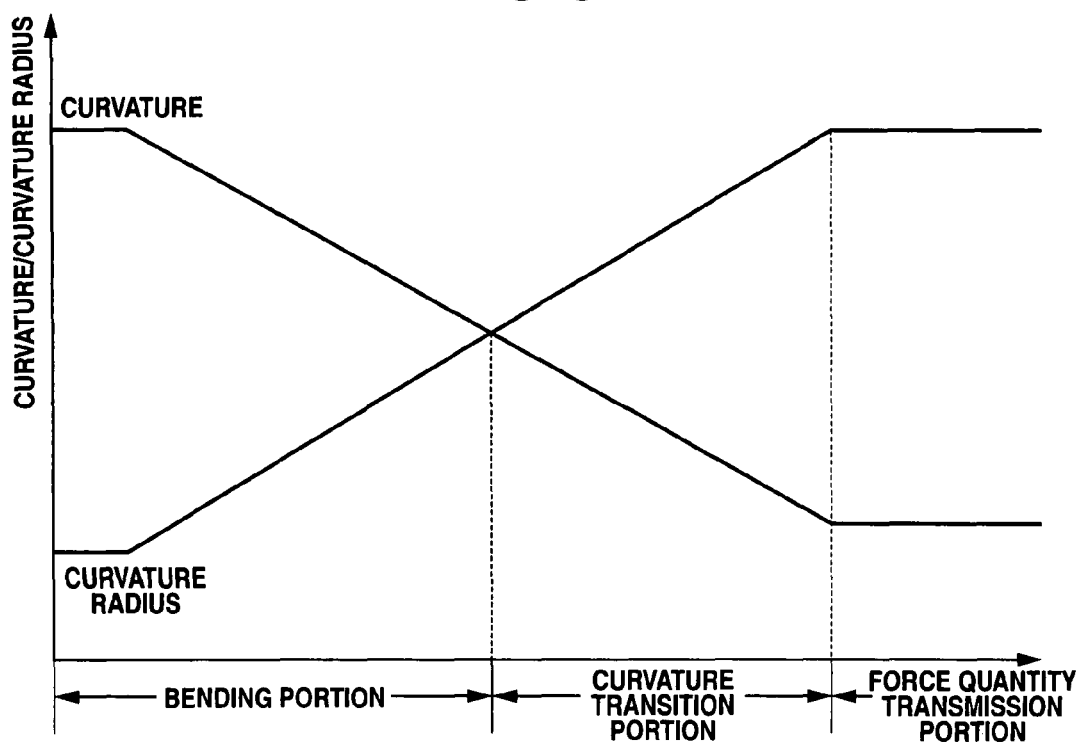
FIG. 32 is a graph representing each change in the curvature and the curvature radius of the bending portion, the curvature transition portion and the flexible tube portion of the insertion portion shown in FIG. 30 with respect to the insertion axis.

Referring to the graph shown in FIG. 31, the flexural rigidity of the insertion portion 6 of the endoscope 2 is set to become sequentially higher from the distal end to the proximal end of the respective portions of the bending portion 12 and the curvature transition portion 13 at the constant rate. In other words, the flexural rigidity of the bending portion 12 at the most distal end is the lowest, from where the flexural rigidity is sequentially increased at the constant rate, and then the flexural rigidity of the curvature transition portion 13 at the most proximal end is the highest. The force quantity transmission portion 14 is configured to have the flexural rigidity which is substantially the same as that of the curvature transition portion 13 at the most proximal end over the whole length.

The bending portion 12 which is bent in abutment against the body cavity wall which is flexed under the predetermined pressing force (for example, the force of approximately 2 kg to maximum) has the highest curvature at the insertion axis, from where the curvature sequentially decreases at the constant rate.

The curvature transition portion 13 which is bent in the similar way as described above has the curvature at the insertion axis decreased at the constant rate from the boundary between the second bending portion 12*b* and the first curvature transition portion 13*a* such that the curvature of the most proximal end at the insertion axis becomes the lowest. In other words, the curvature radius of the bending portion 12 at the most distal end at the insertion axis which is bent in abutment on the body cavity wall which flexes under the predetermined pressing force (for example, the force of approximately 2 kg to maximum) is the smallest, from where the curvature radius at the insertion axis sequentially increases to become the largest at the insertion axis of the curvature transition portion 13 at the most proximal end.

When the operator pushes the force quantity transmission portion 14 deep into the large intestine under the predetermined force (for example, the force of approximately 2 kg to maximum) while operating the bending portion 12 to be bent along the flexed portion of the intestine such as the large intestine, the bending portion 12 and the curvature transition portion 13 are bent to follow the flexing of the body cavity in abutment on the flexed body cavity wall. At this time, the curvature transition portion 13 allows the curvature radius at the insertion axis in the bent state to increase at the constant rate along the bending state of the bending portion 12 from the distal end side to the proximal end side.

Accordingly, the curvature radius at the insertion axis becomes sequentially large at the constant rate from the bending portion 12 to the curvature transmission portion 13. As the curvature radius at the insertion axis of the curvature transition portion 13 is held larger than that of the bending portion 12 at the insertion axis, the force quantity transmission portion 14 may be smoothly inserted into the flexed portion of the intestine.

The bending portion 12, the curvature transition portion 13 and the force quantity transmission portion 14 which pass the flexed portion of the intestine are inserted deep into the large intestine without being stuck with the flexed intestine wall. As the flexural rigidity of the force quantity transmission portion 14 is higher than each flexural rigidity of the bending portion 12 and the curvature transition portion 13, the pressing force applied to the curvature transition portion 13 may be transmitted while keeping its shape.

The insertion portion 6 of the endoscope 2 according to the embodiments has the curvature gently varied from the bending portion 12 to the curvature transition portion 13 so as to pass the flexed portion of the intestine smoothly without bringing the bending portion 12 and the curvature transition portion 13 into the acute bent state. As the resistance generated when the bending portion 12 passes the flexed portion of the large intestine may be kept suppressed, the burden and the pain suffered by the patient who receives the endoscopic inspection using the endoscope 2 according to the embodiment may be reduced.

Figure 33:
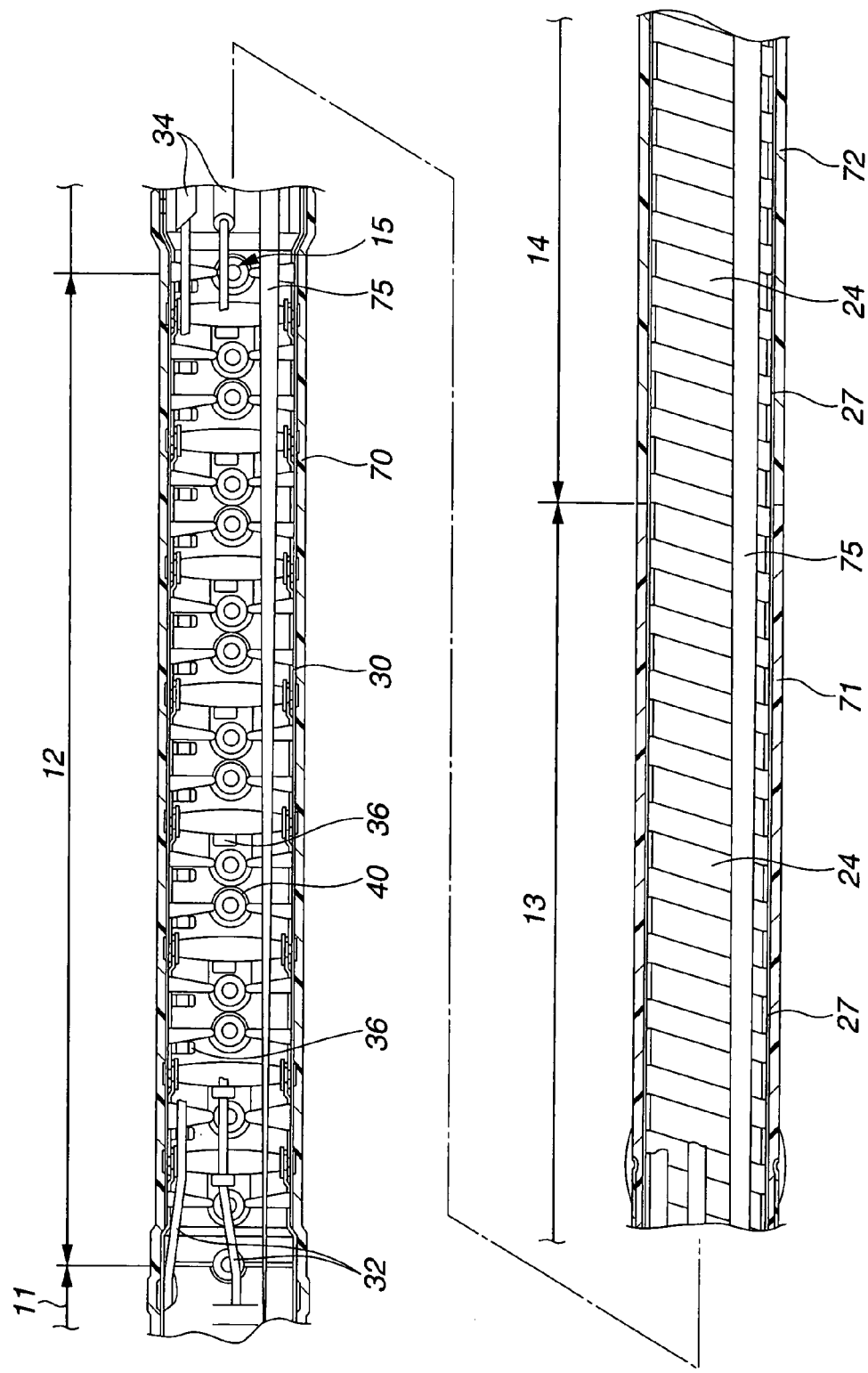
FIG. 33 is a sectional view showing the section of the distal end portion of the insertion portion of the endoscope which has been cut in the longitudinal direction for representing the rigidity adjusting bar in the modified example of the insertion portion shown in FIG. 30.

Referring to FIG. 33, the insertion portion 6 of the endoscope 2 may be provided with a flexural rigidity adjuster bar 75 as a long bar-like member formed of a metal, for example, the nickel-titanium alloy such that the curvature gently varies from the bending portion 12 to the curvature transition portion 13.

The flexural rigidity adjuster bar 75 disposed in the insertion portion 6 is a conical structured which has its external diameter gradually increased from the bending portion 12 to the curvature transition portion 13, and its external diameter kept constant in the range of the force quantity transmission portion 14.

The flexural rigidity adjuster bar 75 has the lowest flexural rigidity at the most distal end of the bending portion 12 so as to be increased at the constant rate until the flexural rigidity at the most proximal end of the curvature transition portion 13 is the highest. The flexural rigidity adjuster bar 75 in the force quantity transmission portion 14 has the constant flexural rigidity which is substantially the same as the one at the most proximal end of the curvature transition portion 13.

The flexural rigidity of the bending portion 12 of the insertion portion 6 at the most distal end is the lowest, which then sequentially increases at the constant rate until each flexural rigidity of the curvature transition portion 13 at the most proximal end and the force quantity transmission portion 14 becomes the highest. In this case, the rigidity of the respective outer coats 70 to 72 takes the same value.

The forceps channel, the coil sheath, and various endoscopic channels may be used instead of the flexural rigidity adjuster bar 75 such that the flexural rigidity of the insertion portion 6 is sequentially increased at the constant rate from the bending portion 12 to the curvature transition portion 13.

In the aforementioned embodiments, the force quantity transmission portion 14 is not provided, but the distal end configuration portion 11, the bending portion 12 and the curvature transition portion 13 may only be provided for the insertion portion 6.

According to the present invention, the resistance generated upon passage of the insertion portion on the flexed portion of the body cavity may be suppressed to improve the performance for inserting the insertion portion 6 as well as realize the endoscope flexible tube and the endoscope device which reduces the burden and the pain suffered by the patient.

The present invention is not limited to the embodiment as described above but may be modified into various forms without departing from the scope of the invention.

The invention claimed is:

1. An endoscope including an insertion portion which exhibits flexibility to be inserted into a body cavity, the endoscope comprising:
   a bending portion formed at a distal end side which is configured to be maximally bent with a first curvature radius and to be bendable according to a bending operation by an operator, the bending portion being provided inside thereof a plurality of annular bending pieces which are rotatably connected in series by pivots, peripheral edges of opposite surfaces of adjacent ones of the bending pieces serving as abutment portions to abut to each other to regulate the curvature radius at which the bending portion is maximally bent;
   a first flexible tube portion connected in series at a proximal end side of the bending portion, which is maximally bendable with a second curvature radius larger than the first curvature radius, and which is bent when applied with an external force but is not bendable according to a bending operation by an operator, the first flexible tube portion being maximally bent by being pushed against an inner wall of the body cavity, the first flexible tube portion being provided inside thereof a plurality of curvature regulation pieces rotatably connected in series by pivots, peripheral edges of opposite surfaces of adjacent ones of the curvature regulation pieces serving as abutment portions to abut to each other to regulate the curvature radius at which the first flexible tube is maximally bent; and
   a second flexible tube portion connected in series at a proximal end side of the first flexible tube portion, the second flexible tube portion comprising a helical tube, a braid covering an outer circumference of the helical tube, and an outer resin coat covering the braid, the second flexible tube portion having a flexural rigidity larger than a flexural rigidity of the first flexible tube portion.

2. The endoscope according to claim 1, wherein the first flexible tube is formed such that the curvature radius of the first flexible tube when maximally bent is larger at a side of the second flexible tube portion than at a side of the bending portion.

3. The endoscope according to claim 2, wherein the curvature radius of the first flexible tube portion when maximally bent is set to vary stepwise or continuously from the side of the bending portion to the side of the second flexible tube portion.

4. The endoscope according to claim 1, wherein, in a state where an insertion axis of the bending portion and the first flexible tube is in a linear state, a distance between each of the pivots that rotatably connect in series the plurality of curvature regulation pieces provided in the first flexible tube portion and an angle between the abutment portions opposing to each other of the curvature regulation pieces adjacent to each other with a rotation center of each of the pivots serving as an apex are set relative to a distance between each of the pivots that rotatably connect in series the plurality of bending pieces provided in the bending portion and an angle between the abutment portions opposing to each other of the bending pieces adjacent to each other with a rotation center of each of the pivots serving as an apex, so that the second curvature radius is larger than the first curvature radius.

* * * * *